US011999796B2

(12) United States Patent
Wang et al.

(10) Patent No.: US 11,999,796 B2
(45) Date of Patent: Jun. 4, 2024

(54) ANTI-CD70 CHIMERIC ANTIGEN RECEPTORS

(71) Applicant: The United States of America, as represented by the Secretary, Department of Health and Human Services, Bethesda, MD (US)

(72) Inventors: Qiong J. Wang, Potomac, MD (US); Zhiya Yu, Potomac, MD (US); James C. Yang, Bethesda, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 750 days.

(21) Appl. No.: 16/906,061

(22) Filed: Jun. 19, 2020

(65) Prior Publication Data

US 2020/0317807 A1    Oct. 8, 2020

Related U.S. Application Data

(62) Division of application No. 15/531,626, filed as application No. PCT/US2015/025047 on Apr. 9, 2015, now Pat. No. 10,689,456.

(60) Provisional application No. 62/088,882, filed on Dec. 8, 2014.

(51) Int. Cl.
*A61K 35/17* (2015.01)
*A61P 35/00* (2006.01)
*C07K 14/705* (2006.01)
*C07K 14/715* (2006.01)
*C07K 14/725* (2006.01)
*C07K 16/28* (2006.01)
*C07K 16/30* (2006.01)

(52) U.S. Cl.
CPC .............. *C07K 16/30* (2013.01); *A61P 35/00* (2018.01); *C07K 14/7051* (2013.01); *C07K 14/70517* (2013.01); *C07K 14/70521* (2013.01); *C07K 14/70578* (2013.01); *C07K 14/7153* (2013.01); *C07K 16/2875* (2013.01); *A61K 35/17* (2013.01); *C07K 2317/60* (2013.01); *C07K 2317/622* (2013.01); *C07K 2319/00* (2013.01); *C07K 2319/02* (2013.01); *C07K 2319/03* (2013.01); *C07K 2319/33* (2013.01)

(58) Field of Classification Search
CPC .................................... A61K 35/17
See application file for complete search history.

(56) References Cited

U.S. PATENT DOCUMENTS

| 8,034,334 B2 | 10/2011 | Dudley et al. |
| 8,383,099 B2 | 2/2013 | Dudley et al. |
| 8,465,743 B2 | 6/2013 | Rosenberg et al. |
| 2007/0037165 A1 | 2/2007 | Venter et al. |
| 2010/0105136 A1 | 4/2010 | Carter et al. |
| 2012/0244133 A1 | 9/2012 | Rosenberg et al. |
| 2013/0323214 A1 | 12/2013 | Gottschalk et al. |

FOREIGN PATENT DOCUMENTS

| CN | 104159909 A | 11/2014 | |
| JP | 2014-516510 A | 7/2014 | |
| WO | WO 92/01049 A2 | 1/1992 | |
| WO | WO 2012/058460 A2 | 5/2012 | |
| WO | WO 2012/138475 A1 | 10/2012 | |
| WO | WO 2013/059593 A1 | 4/2013 | |
| WO | WO 2013/126712 A1 | 8/2013 | |
| WO | WO 2013/185552 A1 | 12/2013 | |
| WO | WO 2014/055771 A1 | 4/2014 | |
| WO | WO 2014/070957 A1 | 5/2014 | |
| WO | WO-2016093878 A1 * | 6/2016 | ............. A61K 35/17 |

OTHER PUBLICATIONS

Winkler et al. (J. Immunol. Oct. 15, 2005; 165 (8): 4505-4514).*
U.S. Appl. No. 15/531,626, filed May 30, 2017.
Bowie et al., "Deciphering the Message in Protein Sequences: Tolerance to Amino Acid Substitutions," *Science*, 257: 1306-1320 (1990).
Burgess et al., "Possible Dissociation of the Heparin-binding and Mitogenic Activities of Heparin-binding (Acidic Fibroblast) Growth Factor-1 from Its Receptor-binding Activities by Site-directed Mutagensis of a Single Lysine Residue," *Journal of Cell Biology*, 111: 2129-2138 (1990).
Clay et al., "Efficient transfer of a tumor antigen-reactive TCR to human peripheral blood lymphocytes confers anti-tumor reactivity," *The Journal of Immunology*, 163: 507-513 (1999).

(Continued)

*Primary Examiner* — Stephen L Rawlings
(74) *Attorney, Agent, or Firm* — Leydig, Voit & Mayer

(57) ABSTRACT

The invention provides a chimeric antigen receptor (CAR) having antigenic specificity for CD70, the CAR comprising: an antigen binding—transmembrane domain comprising a CD27 amino acid sequence lacking all or a portion of the CD27 intracellular T cell signaling domain; a 4-1BB intracellular T cell signaling domain; a CD3ζ intracellular T cell signaling domain; and optionally, a CD28 intracellular T cell signaling domain. Nucleic acids, recombinant expression vectors, host cells, populations of cells, and pharmaceutical compositions relating to the CARs are disclosed. Methods of detecting the presence of cancer in a mammal and methods of treating or preventing cancer in a mammal are also disclosed.

7 Claims, 5 Drawing Sheets

Specification includes a Sequence Listing.

(56) References Cited

OTHER PUBLICATIONS

English Thomson entry for WO 2013/185552 (Dec. 9, 2013) Database WPI, Week 201405, Thomson Scientific, AN 2013-X28425.
Diegmann et al., "Identification of CD70 as a diagnostic biomarker for clear cell renal cell carcinoma by gene expression profiling, real-time RT-PCR and immunohistochemistry," *European Journal of Cancer* 41: 1794-1801 (2005).
Dudley et al., "Generation of tumor-infiltrating lymphocyte cultures for use in adoptive transfer therapy for melanoma patients," *Journal of Immunotherapy*, 26:332-42 (2003).
Genbank Accession No. NM_001242, *Homo sapiens* CD27 molecule (CD27), May 3, 2014.
Genbank Accession No. NP_000725.1, T-cell surface glycoprotein CD3 zeta chain isoform 2 precursor [*Homo sapiens*], Aug. 12, 2014.
Genbank Accession No. NP_932170.1, T-cell surface glycoprotein CD3 zeta chain isoform 1 precursor [*Homo sapiens*], Aug. 11, 2014.
Guo et al., "Protein tolerance to random amino acid change," *Proc. Natl. Acad. Sci.*, 101(25): 9205-9210 (2004).
Held-Feindt et al., "CD70/CD27 ligand, a member of the TNF family, is expressed in human brain tumors," *International Journal of Cancer*, 98: 352-56 (2002).
International Bureau, International Search Report in International Application No. PCT/US2015/025047, dated Jul. 24, 2015.
International Searching Authority, Written Opinion in International Application No. PCT/US2015/025047, dated Jul. 24, 2015.
Kochenderfer et al., "B-cell depletion and remissions of malignancy along with cytokine-associated toxicity in a clinical trial of anti-CD19 chimeric-antigen-receptor-transduced T cells," *Blood*, 119(12): 2709-2720 (2012).
Lazar et al., "Transforming Growth Factor a: Mutation of Aspartic Acid 47 and Leucine 48 Results in Different Biological Activities," *Molecular and Cellular Biology*, 8: 1247-1252 (1988).
Lens et al., "Aberrant expression and reverse signalling of CD70 on malignant B cells," *British Journal of Haematology*, 106: 491-503 (1999).

Long et al., "4-1BB costimulation ameliorates T cell exhaustion induced by tonic signaling of chimeric antigen receptors," *Nat. Med.*, 21(6): 581-590 (2015).
Milone et al., "Chimeric Receptors Containing CD137 Signal Transduction Domains Mediate Enhanced Survival of T Cells and Increased Antileukemic Efficacy In Vivo," *Mol. Ther.*, 17(8): 1453-1464 (2009).
Riddell et al., "The use of anti-CD3 and anti-CD28 monoclonal antibodies to clone and expand human antigen-specific T cells," *Journal of Immunological Methods*, 128: 189-201 (1990).
Rossig et al., "Genetic Modification of T Lymphocytes for Adoptive Immunotherapy," *Mol. Ther.*, 10(1): 5-18 (2004).
Sadelain et al., "The promise and potential pitfalls of chimeric antigen receptors," *Curr. Opin. Immunol.*, 21: 215-223 (2009).
Shaffer et al., "Foreign or Domestic CARs: Receptor Ligands as Antigen-Binding Domains," *Medical Sciences*, 2: 23-36 (2014).
Shaffer et al., "T cells redirected against CD70 for the immunotherapy of CD70-positive malignancies," *Blood*, 117(16): 4304-4314 (2011).
Song et al., "In Vivo Persistence, Tumor Localization, and Antitumor Activity of CAR-Engineered T Cells is Enhanced by Costimulatory Signaling through CD137 (4-1BB)," *Cancer Res.*, 71(13): 4617-4627 (2011).
Tammana et al., "4-1BB and CD28 Signaling Plays a Synergistic Role in Redirecting Umbilical Cord Blood T Cells Against B-Cell Malignancies," *Hum. Gene Ther.*, 21(1): 75-86 (2010).
Takada et al., "Alteration of a Single Amino Acid in Peroxisome Proliferator-Activated Receptor-α (PPARα) Generates a PPARδ Phenotype," *Mol. Endocrinol.*, 14(5): 733-740 (2000).
Wang et al., "Preclinical Evaluation of Chimeric Antigen Receptors Targeting CD70-Expressing Cancers," *Clin. Cancer Res.*, 23(9):2267-2276 (2017).
Wischhusen et al., "Identification of CD70-mediated apoptosis of immune effector cells as a novel immune escape pathway of human glioblastoma," *Cancer Research*, 62:2592-99 (2002).
Yang et al., "The Puzzle of Immunotherapy and Renal Cancer," presented at the Cancer Immunology and Immunotherapy Conference (Oct. 10, 2014).
Zhao et al., "Primary human lymphocytes transduced with NY-ESO-1 antigen-specific TCR genes recognize and kill diverse human tumor cell lines," *The Journal of Immunology*, 174: 4415-4423 (2005).

\* cited by examiner

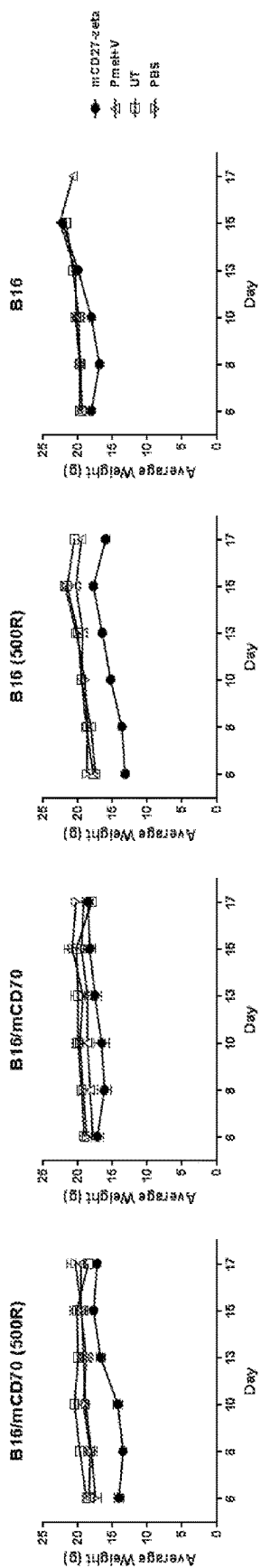
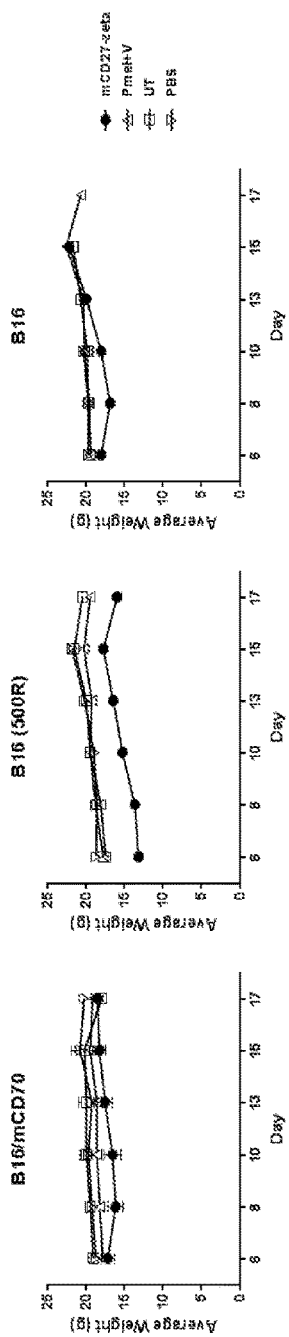
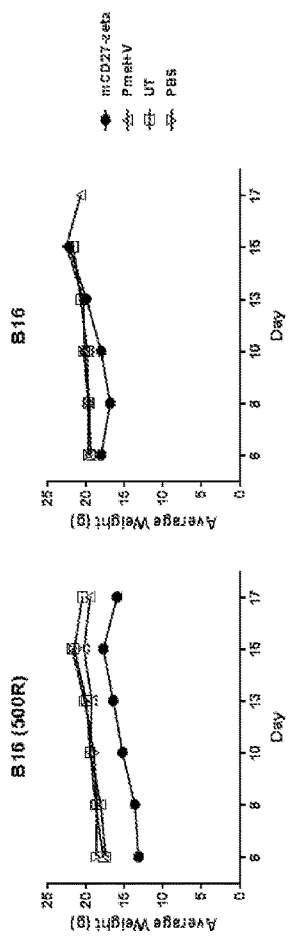
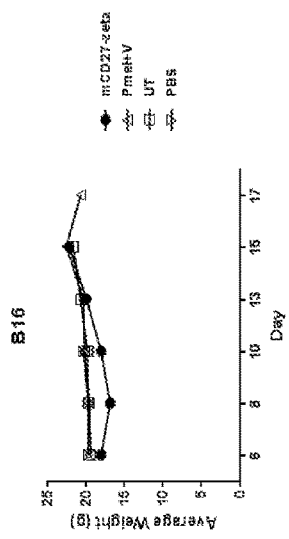
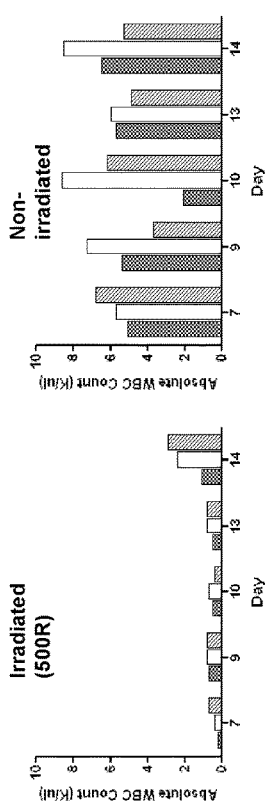
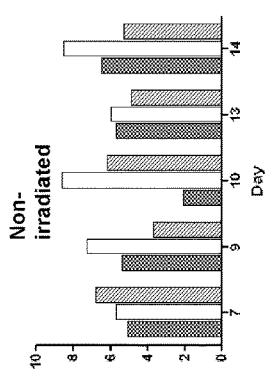
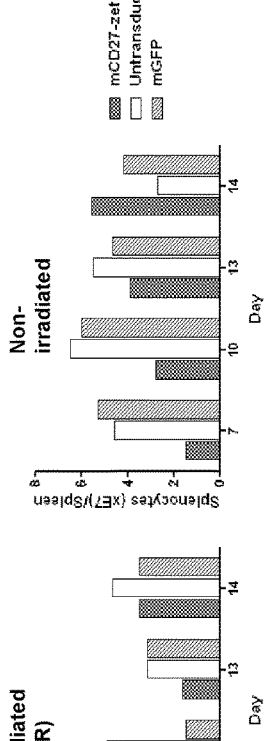
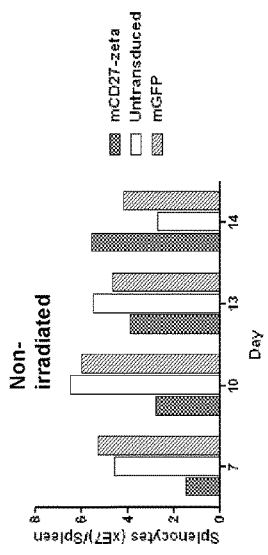
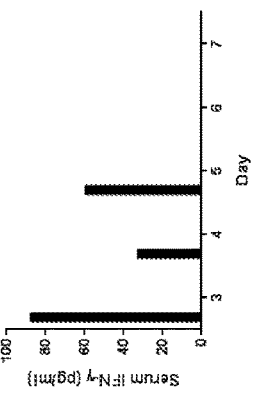

SEQUENCE LISTING

<160> NUMBER OF SEQ ID NOS: 27

<210> SEQ ID NO 1
<211> LENGTH: 193
<212> TYPE: PRT
<213> ORGANISM: Homo sapiens

<400> SEQUENCE: 1

Met Pro Glu Glu Gly Ser Gly Cys Ser Val Arg Arg Arg Pro Tyr Gly
1               5                   10                  15

Cys Val Leu Arg Ala Ala Leu Val Pro Leu Val Ala Gly Leu Val Ile
            20                  25                  30

Cys Leu Val Val Cys Ile Gln Arg Phe Ala Gln Ala Gln Gln Gln Leu
        35                  40                  45

Pro Leu Glu Ser Leu Gly Trp Asp Val Ala Glu Leu Gln Leu Asn His
    50                  55                  60

Thr Gly Pro Gln Gln Asp Pro Arg Leu Tyr Trp Gln Gly Gly Pro Ala
65                  70                  75                  80

Leu Gly Arg Ser Phe Leu His Gly Pro Glu Leu Asp Lys Gly Gln Leu
                85                  90                  95

Arg Ile His Arg Asp Gly Ile Tyr Met Val His Ile Gln Val Thr Leu
            100                 105                 110

Ala Ile Cys Ser Ser Thr Thr Ala Ser Arg His His Pro Thr Thr Leu
        115                 120                 125

Ala Val Gly Ile Cys Ser Pro Ala Ser Arg Ser Ile Ser Leu Leu Arg
    130                 135                 140

Leu Ser Phe His Gln Gly Cys Thr Ile Ala Ser Gln Arg Leu Thr Pro
145                 150                 155                 160

```
Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
            180                 185                 190

Pro

<210> SEQ ID NO 2
<211> LENGTH: 260
<212> TYPE: PRT
<213> ORGANISM: Homo sapiens

<400> SEQUENCE: 2

Met Ala Arg Pro His Pro Trp Trp Leu Cys Val Leu Gly Thr Leu Val
1               5                   10                  15

Gly Leu Ser Ala Thr Pro Ala Pro Lys Ser Cys Pro Glu Arg His Tyr
            20                  25                  30

Trp Ala Gln Gly Lys Leu Cys Cys Gln Met Cys Glu Pro Gly Thr Phe
        35                  40                  45

Leu Val Lys Asp Cys Asp Gln His Arg Lys Ala Ala Gln Cys Asp Pro
    50                  55                  60

Cys Ile Pro Gly Val Ser Phe Ser Pro Asp His His Thr Arg Pro His
65                  70                  75                  80

Cys Glu Ser Cys Arg His Cys Asn Ser Gly Leu Leu Val Arg Asn Cys
                85                  90                  95

Thr Ile Thr Ala Asn Ala Glu Cys Ala Cys Arg Asn Gly Trp Gln Cys
            100                 105                 110

Arg Asp Lys Glu Cys Thr Glu Cys Asp Pro Leu Pro Asn Pro Ser Leu
        115                 120                 125

Thr Ala Arg Ser Ser Gln Ala Leu Ser Pro His Pro Gln Pro Thr His
    130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
                165                 170                 175

His Trp Pro Pro Gln Arg Ser Leu Cys Ser Ser Asp Phe Ile Arg Ile
            180                 185                 190

Leu Val Ile Phe Ser Gly Met Phe Leu Val Phe Thr Leu Ala Gly Ala
        195                 200                 205

Leu Phe Leu His Gln Arg Arg Lys Tyr Arg Ser Asn Lys Gly Glu Ser
    210                 215                 220

Pro Val Glu Pro Ala Glu Pro Cys Arg Tyr Ser Cys Pro Arg Glu Glu
225                 230                 235                 240

Glu Gly Ser Thr Ile Pro Ile Gln Glu Asp Tyr Arg Lys Pro Glu Pro
                245                 250                 255

Ala Cys Ser Pro
            260

<210> SEQ ID NO 3
<211> LENGTH: 211
<212> TYPE: PRT
<213> ORGANISM: Homo sapiens

<400> SEQUENCE: 3

Met Ala Arg Pro His Pro Trp Trp Leu Cys Val Leu Gly Thr Leu Val
1               5                   10                  15
```

```
Gly Leu Ser Ala Thr Pro Ala Pro Lys Ser Cys Pro Glu Arg His Tyr
            20                  25                  30

Trp Ala Gln Gly Lys Leu Cys Cys Gln Met Cys Glu Pro Gly Thr Phe
        35                  40                  45

Leu Val Lys Asp Cys Asp Gln His Arg Lys Ala Ala Gln Cys Asp Pro
    50                  55                  60

Cys Ile Pro Gly Val Ser Phe Ser Pro Asp His His Thr Arg Pro His
65                  70                  75                  80

Cys Glu Ser Cys Arg His Cys Asn Ser Gly Leu Leu Val Arg Asn Cys
                85                  90                  95

Thr Ile Thr Ala Asn Ala Glu Cys Ala Cys Arg Asn Gly Trp Gln Cys
            100                 105                 110

Arg Asp Lys Glu Cys Thr Glu Cys Asp Pro Leu Pro Asn Pro Ser Leu
        115                 120                 125

Thr Ala Arg Ser Ser Gln Ala Leu Ser Pro His Pro Gln Pro Thr His
    130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
                165                 170                 175

His Trp Pro Pro Gln Arg Ser Leu Cys Ser Ser Asp Phe Ile Arg Ile
            180                 185                 190

Leu Val Ile Phe Ser Gly Met Phe Leu Val Phe Thr Leu Ala Gly Ala
        195                 200                 205

Leu Phe Leu
    210

<210> SEQ ID NO 4
<211> LENGTH: 112
<212> TYPE: PRT
<213> ORGANISM: Homo sapiens

<400> SEQUENCE: 4

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 5
<211> LENGTH: 47
<212> TYPE: PRT
<213> ORGANISM: Homo sapiens

<400> SEQUENCE: 5

Arg Phe Ser Val Val Lys Arg Gly Arg Lys Lys Leu Leu Tyr Ile Phe
1               5                   10                  15
```

-continued

```
Lys Gln Pro Phe Met Arg Pro Val Gln Thr Thr Gln Glu Glu Asp Gly
             20                  25                  30

Cys Ser Cys Arg Phe Pro Glu Glu Glu Gly Gly Cys Glu Leu
         35                  40                  45

<210> SEQ ID NO 6
<211> LENGTH: 41
<212> TYPE: PRT
<213> ORGANISM: Homo sapiens

<400> SEQUENCE: 6

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
             20                  25                  30

Pro Arg Asp Phe Ala Ala Tyr Arg Ser
         35                  40

<210> SEQ ID NO 7
<211> LENGTH: 372
<212> TYPE: PRT
<213> ORGANISM: Artificial Sequence
<220> FEATURE:
<223> OTHER INFORMATION: Synthetic

<400> SEQUENCE: 7

Met Ala Arg Pro His Pro Trp Trp Leu Cys Val Leu Gly Thr Leu Val
1               5                   10                  15

Gly Leu Ser Ala Thr Pro Ala Pro Lys Ser Cys Pro Glu Arg His Tyr
             20                  25                  30

Trp Ala Gln Gly Lys Leu Cys Cys Gln Met Cys Glu Pro Gly Thr Phe
         35                  40                  45

Leu Val Lys Asp Cys Asp Gln His Arg Lys Ala Ala Gln Cys Asp Pro
     50                  55                  60

Cys Ile Pro Gly Val Ser Phe Ser Pro Asp His His Thr Arg Pro His
65                  70                  75                  80

Cys Glu Ser Cys Arg His Cys Asn Ser Gly Leu Leu Val Arg Asn Cys
                 85                  90                  95

Thr Ile Thr Ala Asn Ala Glu Cys Ala Cys Arg Asn Gly Trp Gln Cys
             100                 105                 110

Arg Asp Lys Glu Cys Thr Glu Cys Asp Pro Leu Pro Asn Pro Ser Leu
         115                 120                 125

Thr Ala Arg Ser Ser Gln Ala Leu Ser Pro His Pro Gln Pro Thr His
     130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
                 165                 170                 175

His Trp Pro Pro Gln Arg Ser Leu Cys Ser Ser Asp Phe Ile Arg Ile
             180                 185                 190

Leu Val Ile Phe Ser Gly Met Phe Leu Val Phe Thr Leu Ala Gly Ala
         195                 200                 205

Leu Phe Leu His Gln Arg Arg Lys Tyr Arg Ser Asn Lys Gly Glu Ser
     210                 215                 220

Pro Val Glu Pro Ala Glu Pro Cys Arg Tyr Ser Cys Pro Arg Glu Glu
225                 230                 235                 240

Glu Gly Ser Thr Ile Pro Ile Gln Glu Asp Tyr Arg Lys Pro Glu Pro
```

```
                   245                 250                 255
Ala Cys Ser Pro Arg Val Lys Phe Ser Arg Ser Ala Asp Ala Pro Ala
                260                 265                 270

Tyr Gln Gln Gly Gln Asn Gln Leu Tyr Asn Glu Leu Asn Leu Gly Arg
            275                 280                 285

Arg Glu Glu Tyr Asp Val Leu Asp Lys Arg Gly Arg Asp Pro Glu
        290                 295                 300

Met Gly Gly Lys Pro Arg Arg Lys Asn Pro Gln Glu Gly Leu Tyr Asn
305                 310                 315                 320

Glu Leu Gln Lys Asp Lys Met Ala Glu Ala Tyr Ser Glu Ile Gly Met
                325                 330                 335

Lys Gly Glu Arg Arg Arg Gly Lys Gly His Asp Gly Leu Tyr Gln Gly
                340                 345                 350

Leu Ser Thr Ala Thr Lys Asp Thr Tyr Asp Ala Leu His Met Gln Ala
            355                 360                 365

Leu Pro Pro Arg
   370

<210> SEQ ID NO 8
<211> LENGTH: 364
<212> TYPE: PRT
<213> ORGANISM: Artificial Sequence
<220> FEATURE:
<223> OTHER INFORMATION: Synthetic

<400> SEQUENCE: 8

Met Ala Arg Pro His Pro Trp Trp Leu Cys Val Leu Gly Thr Leu Val
1               5                   10                  15

Gly Leu Ser Ala Thr Pro Ala Pro Lys Ser Cys Pro Glu Arg His Tyr
                20                  25                  30

Trp Ala Gln Gly Lys Leu Cys Cys Gln Met Cys Glu Pro Gly Thr Phe
            35                  40                  45

Leu Val Lys Asp Cys Asp Gln His Arg Lys Ala Ala Gln Cys Asp Pro
        50                  55                  60

Cys Ile Pro Gly Val Ser Phe Ser Pro Asp His His Thr Arg Pro His
65                  70                  75                  80

Cys Glu Ser Cys Arg His Cys Asn Ser Gly Leu Leu Val Arg Asn Cys
                85                  90                  95

Thr Ile Thr Ala Asn Ala Glu Cys Ala Cys Arg Asn Gly Trp Gln Cys
            100                 105                 110

Arg Asp Lys Glu Cys Thr Glu Cys Asp Pro Leu Pro Asn Pro Ser Leu
        115                 120                 125

Thr Ala Arg Ser Ser Gln Ala Leu Ser Pro His Pro Gln Pro Thr His
    130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
                165                 170                 175

His Trp Pro Pro Gln Arg Ser Leu Cys Ser Ser Asp Phe Ile Arg Ile
            180                 185                 190

Leu Val Ile Phe Ser Gly Met Phe Leu Val Phe Thr Leu Ala Gly Ala
        195                 200                 205

Leu Phe Leu Arg Ser Lys Arg Ser Arg Leu Leu His Ser Asp Tyr Met
    210                 215                 220

Asn Met Thr Pro Arg Arg Pro Gly Pro Thr Arg Lys His Tyr Gln Pro
```

```
              225                 230                 235                 240
Tyr Ala Pro Pro Arg Asp Phe Ala Ala Tyr Arg Ser Arg Val Lys Phe
                    245                 250                 255

Ser Arg Ser Ala Asp Ala Pro Ala Tyr Gln Gln Gly Gln Asn Gln Leu
                260                 265                 270

Tyr Asn Glu Leu Asn Leu Gly Arg Glu Glu Tyr Asp Val Leu Asp
            275                 280                 285

Lys Arg Arg Gly Arg Asp Pro Glu Met Gly Gly Lys Pro Arg Arg Lys
        290                 295                 300

Asn Pro Gln Glu Gly Leu Tyr Asn Glu Leu Gln Lys Asp Lys Met Ala
305                 310                 315                 320

Glu Ala Tyr Ser Glu Ile Gly Met Lys Gly Glu Arg Arg Arg Gly Lys
                325                 330                 335

Gly His Asp Gly Leu Tyr Gln Gly Leu Ser Thr Ala Thr Lys Asp Thr
                340                 345                 350

Tyr Asp Ala Leu His Met Gln Ala Leu Pro Pro Arg
            355                 360

<210> SEQ ID NO 9
<211> LENGTH: 370
<212> TYPE: PRT
<213> ORGANISM: Artificial Sequence
<220> FEATURE:
<223> OTHER INFORMATION: Synthetic

<400> SEQUENCE: 9

Met Ala Arg Pro His Pro Trp Trp Leu Cys Val Leu Gly Thr Leu Val
1               5                  10                  15

Gly Leu Ser Ala Thr Pro Ala Pro Lys Ser Cys Pro Glu Arg His Tyr
                20                  25                  30

Trp Ala Gln Gly Lys Leu Cys Cys Gln Met Cys Glu Pro Gly Thr Phe
            35                  40                  45

Leu Val Lys Asp Cys Asp Gln His Arg Lys Ala Ala Gln Cys Asp Pro
        50                  55                  60

Cys Ile Pro Gly Val Ser Phe Ser Pro Asp His His Thr Arg Pro His
65                  70                  75                  80

Cys Glu Ser Cys Arg His Cys Asn Ser Gly Leu Leu Val Arg Asn Cys
                85                  90                  95

Thr Ile Thr Ala Asn Ala Glu Cys Ala Cys Arg Asn Gly Trp Gln Cys
                100                 105                 110

Arg Asp Lys Glu Cys Thr Glu Cys Asp Pro Leu Pro Asn Pro Ser Leu
            115                 120                 125

Thr Ala Arg Ser Ser Gln Ala Leu Ser Pro His Pro Gln Pro Thr His
        130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
                165                 170                 175

His Trp Pro Pro Gln Arg Ser Leu Cys Ser Ser Asp Phe Ile Arg Ile
            180                 185                 190

Leu Val Ile Phe Ser Gly Met Phe Leu Val Phe Thr Leu Ala Gly Ala
        195                 200                 205

Leu Phe Leu Arg Phe Ser Val Val Lys Arg Gly Arg Lys Lys Leu Leu
        210                 215                 220

Tyr Ile Phe Lys Gln Pro Phe Met Arg Pro Val Gln Thr Thr Gln Glu
```

-continued

```
              225                 230                 235                 240
        Glu Asp Gly Cys Ser Cys Arg Phe Pro Glu Glu Glu Gly Gly Cys
                        245                 250                 255
        Glu Leu Arg Val Lys Phe Ser Arg Ser Ala Asp Ala Pro Ala Tyr Gln
                        260                 265                 270
        Gln Gly Gln Asn Gln Leu Tyr Asn Glu Leu Asn Leu Gly Arg Arg Glu
                        275                 280                 285
        Glu Tyr Asp Val Leu Asp Lys Arg Arg Gly Arg Asp Pro Glu Met Gly
                 290                 295                 300
        Gly Lys Pro Arg Arg Lys Asn Pro Gln Glu Gly Leu Tyr Asn Glu Leu
        305                 310                 315                 320
        Gln Lys Asp Lys Met Ala Glu Ala Tyr Ser Glu Ile Gly Met Lys Gly
                        325                 330                 335
        Glu Arg Arg Arg Gly Lys Gly His Asp Gly Leu Tyr Gln Gly Leu Ser
                        340                 345                 350
        Thr Ala Thr Lys Asp Thr Tyr Asp Ala Leu His Met Gln Ala Leu Pro
                        355                 360                 365
        Pro Arg
                370

<210> SEQ ID NO 10
<211> LENGTH: 411
<212> TYPE: PRT
<213> ORGANISM: Artificial Sequence
<220> FEATURE:
<223> OTHER INFORMATION: Synthetic

<400> SEQUENCE: 10

Met Ala Arg Pro His Pro Trp Trp Leu Cys Val Leu Gly Thr Leu Val
        1               5                   10                  15
        Gly Leu Ser Ala Thr Pro Ala Pro Lys Ser Cys Pro Glu Arg His Tyr
                        20                  25                  30
        Trp Ala Gln Gly Lys Leu Cys Cys Gln Met Cys Glu Pro Gly Thr Phe
                        35                  40                  45
        Leu Val Lys Asp Cys Asp Gln His Arg Lys Ala Ala Gln Cys Asp Pro
                50                  55                  60
        Cys Ile Pro Gly Val Ser Phe Ser Pro Asp His His Thr Arg Pro His
        65                  70                  75                  80
        Cys Glu Ser Cys Arg His Cys Asn Ser Gly Leu Leu Val Arg Asn Cys
                        85                  90                  95
        Thr Ile Thr Ala Asn Ala Glu Cys Ala Cys Arg Asn Gly Trp Gln Cys
                        100                 105                 110
        Arg Asp Lys Glu Cys Thr Glu Cys Asp Pro Leu Pro Asn Pro Ser Leu
                        115                 120                 125
        Thr Ala Arg Ser Ser Gln Ala Leu Ser Pro His Pro Gln Pro Thr His
                130                 135                 140
        Leu Pro Tyr Val Ser Glu Met Leu Glu Ala Arg Thr Ala Gly His Met
        145                 150                 155                 160
        Gln Thr Leu Ala Asp Phe Arg Gln Leu Pro Ala Arg Thr Leu Ser Thr
                        165                 170                 175
        His Trp Pro Pro Gln Arg Ser Leu Cys Ser Ser Asp Phe Ile Arg Ile
                        180                 185                 190
        Leu Val Ile Phe Ser Gly Met Phe Leu Val Phe Thr Leu Ala Gly Ala
                        195                 200                 205
        Leu Phe Leu Arg Ser Lys Arg Ser Arg Leu Leu His Ser Asp Tyr Met
```

```
                210                 215                 220
Asn Met Thr Pro Arg Arg Pro Gly Pro Thr Arg Lys His Tyr Gln Pro
225                 230                 235                 240

Tyr Ala Pro Pro Arg Asp Phe Ala Ala Tyr Arg Ser Arg Phe Ser Val
                245                 250                 255

Val Lys Arg Gly Arg Lys Lys Leu Leu Tyr Ile Phe Lys Gln Pro Phe
                260                 265                 270

Met Arg Pro Val Gln Thr Thr Gln Glu Glu Asp Gly Cys Ser Cys Arg
                275                 280                 285

Phe Pro Glu Glu Glu Glu Gly Gly Cys Glu Leu Arg Val Lys Phe Ser
290                 295                 300

Arg Ser Ala Asp Ala Pro Ala Tyr Gln Gln Gly Gln Asn Gln Leu Tyr
305                 310                 315                 320

Asn Glu Leu Asn Leu Gly Arg Arg Glu Glu Tyr Asp Val Leu Asp Lys
                325                 330                 335

Arg Arg Gly Arg Asp Pro Glu Met Gly Gly Lys Pro Arg Arg Lys Asn
                340                 345                 350

Pro Gln Glu Gly Leu Tyr Asn Glu Leu Gln Lys Asp Lys Met Ala Glu
                355                 360                 365

Ala Tyr Ser Glu Ile Gly Met Lys Gly Glu Arg Arg Arg Gly Lys Gly
                370                 375                 380

His Asp Gly Leu Tyr Gln Gly Leu Ser Thr Ala Thr Lys Asp Thr Tyr
385                 390                 395                 400

Asp Ala Leu His Met Gln Ala Leu Pro Pro Arg
                405                 410

<210> SEQ ID NO 11
<211> LENGTH: 413
<212> TYPE: PRT
<213> ORGANISM: Artificial Sequence
<220> FEATURE:
<223> OTHER INFORMATION: Synthetic

<400> SEQUENCE: 11

Met Ala Arg Pro His Pro Trp Trp Leu Cys Val Leu Gly Thr Leu Val
1               5                   10                  15

Gly Leu Ser Ala Thr Pro Ala Pro Lys Ser Cys Pro Glu Arg His Tyr
                20                  25                  30

Trp Ala Gln Gly Lys Leu Cys Cys Gln Met Cys Glu Pro Gly Thr Phe
            35                  40                  45

Leu Val Lys Asp Cys Asp Gln His Arg Lys Ala Ala Gln Cys Asp Pro
        50                  55                  60

Cys Ile Pro Gly Val Ser Phe Ser Pro Asp His His Thr Arg Pro His
65                  70                  75                  80

Cys Glu Ser Cys Arg His Cys Asn Ser Gly Leu Leu Val Arg Asn Cys
                85                  90                  95

Thr Ile Thr Ala Asn Ala Glu Cys Ala Cys Arg Asn Gly Trp Gln Cys
                100                 105                 110

Arg Asp Lys Glu Cys Thr Glu Cys Asp Pro Leu Pro Asn Pro Ser Leu
            115                 120                 125

Thr Ala Arg Ser Ser Gln Ala Leu Ser Pro His Pro Gln Pro Thr His
        130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
```

165                 170                 175
His Trp Pro Pro Gln Arg Ser Leu Cys Ser Ser Asp Phe Ile Arg Ile
            180                 185                 190

Leu Val Ile Phe Ser Gly Met Phe Leu Val Phe Thr Leu Ala Gly Ala
        195                 200                 205

Leu Phe Leu His Gln Arg Arg Lys Tyr Arg Ser Asn Lys Gly Glu Ser
    210                 215                 220

Pro Val Glu Pro Ala Glu Pro Cys Arg Tyr Ser Cys Pro Arg Glu Glu
225                 230                 235                 240

Glu Gly Ser Thr Ile Pro Ile Gln Glu Asp Tyr Arg Lys Pro Glu Pro
                245                 250                 255

Ala Cys Ser Pro Arg Ser Lys Arg Ser Arg Leu Leu His Ser Asp Tyr
            260                 265                 270

Met Asn Met Thr Pro Arg Arg Pro Gly Pro Thr Arg Lys His Tyr Gln
        275                 280                 285

Pro Tyr Ala Pro Pro Arg Asp Phe Ala Ala Tyr Arg Ser Arg Val Lys
    290                 295                 300

Phe Ser Arg Ser Ala Asp Ala Pro Ala Tyr Gln Gln Gly Gln Asn Gln
305                 310                 315                 320

Leu Tyr Asn Glu Leu Asn Leu Gly Arg Arg Glu Glu Tyr Asp Val Leu
                325                 330                 335

Asp Lys Arg Arg Gly Arg Asp Pro Glu Met Gly Gly Lys Pro Arg Arg
            340                 345                 350

Lys Asn Pro Gln Glu Gly Leu Tyr Asn Glu Leu Gln Lys Asp Lys Met
        355                 360                 365

Ala Glu Ala Tyr Ser Glu Ile Gly Met Lys Gly Glu Arg Arg Arg Gly
    370                 375                 380

Lys Gly His Asp Gly Leu Tyr Gln Gly Leu Ser Thr Ala Thr Lys Asp
385                 390                 395                 400

Thr Tyr Asp Ala Leu His Met Gln Ala Leu Pro Pro Arg
                405                 410

<210> SEQ ID NO 12
<211> LENGTH: 419
<212> TYPE: PRT
<213> ORGANISM: Artificial Sequence
<220> FEATURE:
<223> OTHER INFORMATION: Synthetic

<400> SEQUENCE: 12

Met Ala Arg Pro His Pro Trp Trp Leu Cys Val Leu Gly Thr Leu Val
1               5                   10                  15

Gly Leu Ser Ala Thr Pro Ala Pro Lys Ser Cys Pro Glu Arg His Tyr
            20                  25                  30

Trp Ala Gln Gly Lys Leu Cys Cys Gln Met Cys Glu Pro Gly Thr Phe
        35                  40                  45

Leu Val Lys Asp Cys Asp Gln His Arg Lys Ala Ala Gln Cys Asp Pro
    50                  55                  60

Cys Ile Pro Gly Val Ser Phe Ser Pro Asp His His Thr Arg Pro His
65                  70                  75                  80

Cys Glu Ser Cys Arg His Cys Asn Ser Gly Leu Leu Val Arg Asn Cys
                85                  90                  95

Thr Ile Thr Ala Asn Ala Glu Cys Ala Cys Arg Asn Gly Trp Gln Cys
            100                 105                 110

Arg Asp Lys Glu Cys Thr Glu Cys Asp Pro Leu Pro Asn Pro Ser Leu

```
            115                 120                 125
Thr Ala Arg Ser Ser Gln Ala Leu Ser Pro His Pro Gln Pro Thr His
            130                 135                 140
Leu Pro Tyr Val Ser Glu Met Leu Glu Ala Arg Thr Ala Gly His Met
145                 150                 155                 160
Gln Thr Leu Ala Asp Phe Arg Gln Leu Pro Ala Arg Thr Leu Ser Thr
                165                 170                 175
His Trp Pro Pro Gln Arg Ser Leu Cys Ser Ser Asp Phe Ile Arg Ile
            180                 185                 190
Leu Val Ile Phe Ser Gly Met Phe Leu Val Phe Thr Leu Ala Gly Ala
            195                 200                 205
Leu Phe Leu His Gln Arg Arg Lys Tyr Arg Ser Asn Lys Gly Glu Ser
            210                 215                 220
Pro Val Glu Pro Ala Glu Pro Cys Arg Tyr Ser Cys Pro Arg Glu Glu
225                 230                 235                 240
Glu Gly Ser Thr Ile Pro Ile Gln Glu Asp Tyr Arg Lys Pro Glu Pro
                245                 250                 255
Ala Cys Ser Pro Arg Phe Ser Val Val Lys Arg Gly Arg Lys Lys Leu
                260                 265                 270
Leu Tyr Ile Phe Lys Gln Pro Phe Met Arg Pro Val Gln Thr Thr Gln
            275                 280                 285
Glu Glu Asp Gly Cys Ser Cys Arg Phe Pro Glu Glu Glu Glu Gly Gly
            290                 295                 300
Cys Glu Leu Arg Val Lys Phe Ser Arg Ser Ala Asp Ala Pro Ala Tyr
305                 310                 315                 320
Gln Gln Gly Gln Asn Gln Leu Tyr Asn Glu Leu Asn Leu Gly Arg Arg
                325                 330                 335
Glu Glu Tyr Asp Val Leu Asp Lys Arg Arg Gly Arg Asp Pro Glu Met
                340                 345                 350
Gly Gly Lys Pro Arg Arg Lys Asn Pro Gln Glu Gly Leu Tyr Asn Glu
            355                 360                 365
Leu Gln Lys Asp Lys Met Ala Glu Ala Tyr Ser Glu Ile Gly Met Lys
            370                 375                 380
Gly Glu Arg Arg Arg Gly Lys Gly His Asp Gly Leu Tyr Gln Gly Leu
385                 390                 395                 400
Ser Thr Ala Thr Lys Asp Thr Tyr Asp Ala Leu His Met Gln Ala Leu
                405                 410                 415
Pro Pro Arg

<210> SEQ ID NO 13
<211> LENGTH: 460
<212> TYPE: PRT
<213> ORGANISM: Artificial Sequence
<220> FEATURE:
<223> OTHER INFORMATION: Synthetic

<400> SEQUENCE: 13

Met Ala Arg Pro His Pro Trp Trp Leu Cys Val Leu Gly Thr Leu Val
1               5                   10                  15
Gly Leu Ser Ala Thr Pro Ala Pro Lys Ser Cys Pro Glu Arg His Tyr
                20                  25                  30
Trp Ala Gln Gly Lys Leu Cys Cys Gln Met Cys Glu Pro Gly Thr Phe
            35                  40                  45
Leu Val Lys Asp Cys Asp Gln His Arg Lys Ala Ala Gln Cys Asp Pro
        50                  55                  60
```

```
Cys Ile Pro Gly Val Ser Phe Ser Pro Asp His His Thr Arg Pro His
 65                  70                  75                  80

Cys Glu Ser Cys Arg His Cys Asn Ser Gly Leu Leu Val Arg Asn Cys
             85                  90                  95

Thr Ile Thr Ala Asn Ala Glu Cys Ala Cys Arg Asn Gly Trp Gln Cys
            100                 105                 110

Arg Asp Lys Glu Cys Thr Glu Cys Asp Pro Leu Pro Asn Pro Ser Leu
        115                 120                 125

Thr Ala Arg Ser Ser Gln Ala Leu Ser Pro His Pro Gln Pro Thr His
    130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
                165                 170                 175

His Trp Pro Pro Gln Arg Ser Leu Cys Ser Ser Asp Phe Ile Arg Ile
            180                 185                 190

Leu Val Ile Phe Ser Gly Met Phe Leu Val Phe Thr Leu Ala Gly Ala
        195                 200                 205

Leu Phe Leu His Gln Arg Arg Lys Tyr Arg Ser Asn Lys Gly Glu Ser
    210                 215                 220

Pro Val Glu Pro Ala Glu Pro Cys Arg Tyr Ser Cys Pro Arg Glu Glu
225                 230                 235                 240

Glu Gly Ser Thr Ile Pro Ile Gln Glu Asp Tyr Arg Lys Pro Glu Pro
                245                 250                 255

Ala Cys Ser Pro Arg Ser Lys Arg Ser Arg Leu Leu His Ser Asp Tyr
            260                 265                 270

Met Asn Met Thr Pro Arg Arg Pro Gly Pro Thr Arg Lys His Tyr Gln
        275                 280                 285

Pro Tyr Ala Pro Pro Arg Asp Phe Ala Ala Tyr Arg Ser Arg Phe Ser
    290                 295                 300

Val Val Lys Arg Gly Arg Lys Lys Leu Leu Tyr Ile Phe Lys Gln Pro
305                 310                 315                 320

Phe Met Arg Pro Val Gln Thr Thr Gln Glu Asp Gly Cys Ser Cys
                325                 330                 335

Arg Phe Pro Glu Glu Glu Glu Gly Gly Cys Glu Leu Arg Val Lys Phe
            340                 345                 350

Ser Arg Ser Ala Asp Ala Pro Ala Tyr Gln Gln Gly Gln Asn Gln Leu
        355                 360                 365

Tyr Asn Glu Leu Asn Leu Gly Arg Arg Glu Glu Tyr Asp Val Leu Asp
    370                 375                 380

Lys Arg Arg Gly Arg Asp Pro Glu Met Gly Gly Lys Pro Arg Arg Lys
385                 390                 395                 400

Asn Pro Gln Glu Gly Leu Tyr Asn Glu Leu Gln Lys Asp Lys Met Ala
                405                 410                 415

Glu Ala Tyr Ser Glu Ile Gly Met Lys Gly Glu Arg Arg Arg Gly Lys
            420                 425                 430

Gly His Asp Gly Leu Tyr Gln Gly Leu Ser Thr Ala Thr Lys Asp Thr
        435                 440                 445

Tyr Asp Ala Leu His Met Gln Ala Leu Pro Pro Arg
    450                 455                 460

<210> SEQ ID NO 14
<211> LENGTH: 1119
```

| <212> TYPE: DNA | |
|---|---|
| <213> ORGANISM: Artificial Sequence | |
| <220> FEATURE: | |
| <223> OTHER INFORMATION: Synthetic | |

<400> SEQUENCE: 14

| atggcacggc cacatccctg gtggctgtgc gttctgggga ccctggtggg gctctcagct | 60 |
|---|---|
| actccagccc ccaagagctg cccagagagg cactactggg ctcagggaaa gctgtgctgc | 120 |
| cagatgtgtg agccaggaac attcctcgtg aaggactgtg accagcatag aaaggctgct | 180 |
| cagtgtgatc cttgcatacc gggggtctcc ttctctcctg accaccacac ccggccccac | 240 |
| tgtgagagct gtcggcactg taactctggt cttctcgttc gcaactgcac catcactgcc | 300 |
| aatgctgagt gtgcctgtcg caatggctgg cagtgcaggg acaaggagtg caccgagtgt | 360 |
| gatcctcttc aaacccttc gctgaccgct cggtcgtctc aggccctgag cccacaccct | 420 |
| cagcccaccc acttacctta tgtcagtgag atgctggagg ccaggacagc tgggcacatg | 480 |
| cagactctgg ctgacttcag gcagctgcct gcccggactc tctctaccca ctggccaccc | 540 |
| caaagatccc tgtgcagctc cgattttatt cgcatccttg tgatcttctc tggaatgttc | 600 |
| cttgttttca ccctggccgg ggccctgttc ctccatcaac gaaggaaata tagatcaaac | 660 |
| aaaggagaaa gtcctgtgga gcctgcagag ccttgtcgtt acagctgccc cagggaggag | 720 |
| gagggcagca ccatccccat ccaggaggat taccgaaaac cggagcctgc ctgctccccc | 780 |
| agagtgaagt tcagcaggag cgcagacgcc cccgcgtacc agcagggcca gaaccagctc | 840 |
| tataacgagc tcaatctagg acgaagagag gagtacgatg ttttggacaa gagacgtggc | 900 |
| cgggaccctg agatgggggg aaagccgaga aggaagaacc ctcaggaagg cctgtacaat | 960 |
| gaactgcaga agataagat ggcggaggcc tacagtgaga ttgggatgaa aggcgagcgc | 1020 |
| cggagggca aggggcacga tggcctttac cagggtctca gtacagccac caaggacacc | 1080 |
| tacgacgccc ttcacatgca ggccctgccc cctcgctaa | 1119 |

| <210> SEQ ID NO 15 | |
|---|---|
| <211> LENGTH: 1095 | |
| <212> TYPE: DNA | |
| <213> ORGANISM: Artificial Sequence | |
| <220> FEATURE: | |
| <223> OTHER INFORMATION: Synthetic | |

<400> SEQUENCE: 15

| atggcacggc cacatccctg gtggctgtgc gttctgggga ccctggtggg gctctcagct | 60 |
|---|---|
| actccagccc ccaagagctg cccagagagg cactactggg ctcagggaaa gctgtgctgc | 120 |
| cagatgtgtg agccaggaac attcctcgtg aaggactgtg accagcatag aaaggctgct | 180 |
| cagtgtgatc cttgcatacc gggggtctcc ttctctcctg accaccacac ccggccccac | 240 |
| tgtgagagct gtcggcactg taactctggt cttctcgttc gcaactgcac catcactgcc | 300 |
| aatgctgagt gtgcctgtcg caatggctgg cagtgcaggg acaaggagtg caccgagtgt | 360 |
| gatcctcttc aaacccttc gctgaccgct cggtcgtctc aggccctgag cccacaccct | 420 |
| cagcccaccc acttacctta tgtcagtgag atgctggagg ccaggacagc tgggcacatg | 480 |
| cagactctgg ctgacttcag gcagctgcct gcccggactc tctctaccca ctggccaccc | 540 |
| caaagatccc tgtgcagctc cgattttatt cgcatccttg tgatcttctc tggaatgttc | 600 |
| cttgttttca ccctggccgg ggccctgttc ctccaggagta agaggagcag gctcctgcac | 660 |
| agtgactaca tgaacatgac tccccgccgc cccgggccca cccgcaagca ttaccagccc | 720 |

| | |
|---|---|
| tatgccccac cacgcgactt cgcagcctat cgctccagag tgaagttcag caggagcgca | 780 |
| gacgcccccg cgtaccagca gggccagaac cagctctata cgagctcaa tctaggacga | 840 |
| agagaggagt acgatgtttt ggacaagaga cgtggccggg accctgagat gggggaaag | 900 |
| ccgagaagga agaaccctca ggaaggcctg tacaatgaac tgcagaaaga taagatggcg | 960 |
| gaggcctaca gtgagattgg gatgaaaggc gagcgccgga ggggcaaggg gcacgatggc | 1020 |
| ctttaccagg gtctcagtac agccaccaag gacacctacg acgcccttca catgcaggcc | 1080 |
| ctgccccctc gctaa | 1095 |

```
<210> SEQ ID NO 16
<211> LENGTH: 1113
<212> TYPE: DNA
<213> ORGANISM: Artificial Sequence
<220> FEATURE:
<223> OTHER INFORMATION: Synthetic

<400> SEQUENCE: 16
```

| | |
|---|---|
| atggcacggc cacatccctg gtggctgtgc gttctgggga ccctggtggg gctctcagct | 60 |
| actccagccc ccaagagctg cccagagagg cactactggg ctcagggaaa gctgtgctgc | 120 |
| cagatgtgtg agccaggaac attcctcgtg aaggactgtg accagcatag aaaggctgct | 180 |
| cagtgtgatc cttgcatacc gggggtctcc ttctctcctg accaccacac ccggccccac | 240 |
| tgtgagagct gtcggcactg taactctggt cttctcgttc gcaactgcac catcactgcc | 300 |
| aatgctgagt gtgcctgtcg caatggctgg cagtgcaggg acaaggagtg caccgagtgt | 360 |
| gatcctcttc aaacccttc gctgaccgct cggtcgtctc aggccctgag cccacaccct | 420 |
| cagcccaccc acttacctta tgtcagtgag atgctggagg ccaggacagc tgggcacatg | 480 |
| cagactctgg ctgacttcag gcagctgcct gcccggactc tctctaccca ctggccaccc | 540 |
| caaagatccc tgtgcagctc cgattttatt cgcatccttg tgatcttctc tggaatgttc | 600 |
| cttgttttca ccctggccgg ggccctgttc ctccgtttct ctgttgttaa acggggcaga | 660 |
| aagaagctcc tgtatatatt caaacaacca tttatgagac cagtacaaac tactcaagag | 720 |
| gaagatggct gtagctgccg atttccagaa gaagaagaag gaggatgtga actgagagtg | 780 |
| aagttcagca ggagcgcaga cgcccccgcg taccagcagg gccagaacca gctctataac | 840 |
| gagctcaatc taggacgaag agaggagtac gatgttttgg acaagagacg tggccgggac | 900 |
| cctgagatgg ggggaaagcc gagaaggaag aaccctcagg aaggcctgta caatgaactg | 960 |
| cagaaagata gatggcgga ggcctacagt gagattggga tgaaaggcga gcgccggagg | 1020 |
| ggcaagggc acgatggcct ttaccagggt ctcagtacag ccaccaagga cacctacgac | 1080 |
| gcccttcaca tgcaggccct gccccctcgc taa | 1113 |

```
<210> SEQ ID NO 17
<211> LENGTH: 1236
<212> TYPE: DNA
<213> ORGANISM: Artificial Sequence
<220> FEATURE:
<223> OTHER INFORMATION: Synthetic

<400> SEQUENCE: 17
```

| | |
|---|---|
| atggcacggc cacatccctg gtggctgtgc gttctgggga ccctggtggg gctctcagct | 60 |
| actccagccc ccaagagctg cccagagagg cactactggg ctcagggaaa gctgtgctgc | 120 |
| cagatgtgtg agccaggaac attcctcgtg aaggactgtg accagcatag aaaggctgct | 180 |
| cagtgtgatc cttgcatacc gggggtctcc ttctctcctg accaccacac ccggccccac | 240 |

```
tgtgagagct gtcggcactg taactctggt cttctcgttc gcaactgcac catcactgcc      300
aatgctgagt gtgcctgtcg caatggctgg cagtgcaggg acaaggagtg caccgagtgt      360
gatcctcttc caaacccttc gctgaccgct cggtcgtctc aggccctgag cccacaccct      420
cagcccaccc acttacctta tgtcagtgag atgctggagg ccaggacagc tgggcacatg      480
cagactctgg ctgacttcag gcagctgcct gcccggactc tctctaccca ctggccaccc      540
caaagatccc tgtgcagctc cgattttatt cgcatccttg tgatcttctc tggaatgttc      600
cttgttttca ccctggccgg ggccctgttc ctcaggagta agaggagcag gctcctgcac      660
agtgactaca tgaacatgac tccccgccgc cccgggccca cccgcaagca ttaccagccc      720
tatgccccac cacgcgactt cgcagcctat cgctcccgtt tctctgttgt aaacggggc       780 agaaagaagc tcctgtatat attcaaacaa ccatttatga ccagtacaa aactactcaa        840 gaggaagatg gctgtagctg ccgatttcca gaagaagaag aaggaggatg tgaactgaga      900
gtgaagttca gcaggagcgc agacgccccc gcgtaccagc agggccagaa ccagctctat      960
aacgagctca atctaggacg aagagaggag tacgatgttt tggacaagag acgtggccgg     1020 gacccctgaga tgggggggaaa gccgagaagg aagaaccctc aggaaggcct gtacaatgaa    1080
ctgcagaaag ataagatggc ggaggcctac agtgagattg ggatgaaagg cgagcgccgg     1140
aggggcaagg ggcacgatgg cctttaccag ggtctcagta cagccaccaa ggacacctac     1200
gacgcccttc acatgcaggc cctgcccct cgctaa                                1236
```

<210> SEQ ID NO 18
<211> LENGTH: 1242
<212> TYPE: DNA
<213> ORGANISM: Artificial Sequence
<220> FEATURE:
<223> OTHER INFORMATION: Synthetic

<400> SEQUENCE: 18

```
atggcacggc cacatccctg gtggctgtgc gttctgggga ccctggtggg gctctcagct       60
actccagccc ccaagagctg cccagagagg cactactggg ctcagggaaa gctgtgctgc      120
cagatgtgtg agccaggaac attcctcgtg aaggactgtg accagcatag aaaggctgct      180
cagtgtgatc cttgcatacc gggggtctcc ttctctcctg accaccacac ccggccccac      240
tgtgagagct gtcggcactg taactctggt cttctcgttc gcaactgcac catcactgcc      300
aatgctgagt gtgcctgtcg caatggctgg cagtgcaggg acaaggagtg caccgagtgt      360
gatcctcttc caaacccttc gctgaccgct cggtcgtctc aggccctgag cccacaccct      420
cagcccaccc acttacctta tgtcagtgag atgctggagg ccaggacagc tgggcacatg      480
cagactctgg ctgacttcag gcagctgcct gcccggactc tctctaccca ctggccaccc      540
caaagatccc tgtgcagctc cgattttatt cgcatccttg tgatcttctc tggaatgttc      600
cttgttttca ccctggccgg ggccctgttc ctccatcaac gaaggaaata tagatcaaac      660
aaaggagaaa gtcctgtgga gcctgcagag ccttgtcgtt acagctgccc cagggaggag      720
gagggcagca ccatccccat ccaggaggat taccgaaaac cggagcctgc ctgctccccc      780
aggagtaaga ggagcaggct cctgcacagt gactacatga acatgactcc ccgccgcccc      840
gggcccaccc gcaagcatta ccagccctat gccccaccac gcgacttcgc agcctatcgc      900
tccagagtga agttcagcag gagcgcagac gccccgcgt accagcaggg ccagaaccag       960
ctctataacg agctcaatct aggacgaaga gaggagtacg atgttttgga caagagacgt     1020
```

| | |
|---|---|
| ggccgggacc ctgagatggg gggaaagccg agaaggaaga accctcagga aggcctgtac | 1080 |
| aatgaactgc agaaagataa gatggcggag gcctacagtg agattgggat gaaaggcgag | 1140 |
| cgccggaggg gcaaggggca cgatggcctt taccagggtc tcagtacagc caccaaggac | 1200 |
| acctacgacg cccttcacat gcaggccctg cccctcgct aa | 1242 |

```
<210> SEQ ID NO 19
<211> LENGTH: 1260
<212> TYPE: DNA
<213> ORGANISM: Artificial Sequence
<220> FEATURE:
<223> OTHER INFORMATION: Synthetic

<400> SEQUENCE: 19
```

| | |
|---|---|
| atggcacggc cacatccctg gtggctgtgc gttctgggga ccctggtggg gctctcagct | 60 |
| actccagccc ccaagagctg cccagagagg cactactggg ctcagggaaa gctgtgctgc | 120 |
| cagatgtgtg agccaggaac attcctcgtg aaggactgtg accagcatag aaaggctgct | 180 |
| cagtgtgatc cttgcatacc gggggtctcc ttctctcctg accaccacac ccggccccac | 240 |
| tgtgagagct gtcggcactg taactctggt cttctcgttc gcaactgcac catcactgcc | 300 |
| aatgctgagt gtgcctgtcg caatggctgg cagtgcaggg acaaggagtg caccgagtgt | 360 |
| gatcctcttc caaaccccttc gctgaccgct cggtcgtctc aggccctgag cccacaccct | 420 |
| cagcccaccc acttaccta tgtcagtgag atgctggagg ccaggacagc tgggcacatg | 480 |
| cagactctgg ctgacttcag gcagctgcct gcccggactc tctctaccca ctggccaccc | 540 |
| caaagatccc tgtgcagctc cgatttatt cgcatccttg tgatcttctc tggaatgttc | 600 |
| cttgttttca ccctggccgg ggccctgttc ctccatcaac gaaggaaata tagatcaaac | 660 |
| aaaggagaaa gtcctgtgga gcctgcagag ccttgtcgtt acagctgccc cagggaggag | 720 |
| gagggcagca ccatccccat ccaggaggat taccgaaaac cggagcctgc ctgctccccc | 780 |
| cgtttctctg ttgttaaacg gggcagaaag aagctcctgt atatattcaa acaaccatttt | 840 |
| atgagaccag tacaaactac tcaagaggaa gatggctgta gctgccgatt tccagaagaa | 900 |
| gaagaaggag gatgtgaact gagagtgaag ttcagcagga gcgcagacgc ccccgcgtac | 960 |
| cagcagggcc agaaccagct ctataacgag ctcaatctag gacgaagaga ggagtacgat | 1020 |
| gttttggaca gagacgtgg ccgggaccct gagatggggg gaaagccgag aaggaagaac | 1080 |
| cctcaggaag gcctgtacaa tgaactgcag aaagataaga tggcggaggc ctacagtgag | 1140 |
| attgggatga aaggcgagcg ccggaggggc aaggggcacg atggccttta ccagggtctc | 1200 |
| agtacagcca ccaaggacac ctacgacgcc cttcacatgc aggccctgcc ccctcgctaa | 1260 |

```
<210> SEQ ID NO 20
<211> LENGTH: 1383
<212> TYPE: DNA
<213> ORGANISM: Artificial Sequence
<220> FEATURE:
<223> OTHER INFORMATION: Synthetic

<400> SEQUENCE: 20
```

| | |
|---|---|
| atggcacggc cacatccctg gtggctgtgc gttctgggga ccctggtggg gctctcagct | 60 |
| actccagccc ccaagagctg cccagagagg cactactggg ctcagggaaa gctgtgctgc | 120 |
| cagatgtgtg agccaggaac attcctcgtg aaggactgtg accagcatag aaaggctgct | 180 |
| cagtgtgatc cttgcatacc gggggtctcc ttctctcctg accaccacac ccggccccac | 240 |
| tgtgagagct gtcggcactg taactctggt cttctcgttc gcaactgcac catcactgcc | 300 |

```
aatgctgagt gtgcctgtcg caatggctgg cagtgcaggg acaaggagtg caccgagtgt    360
gatcctcttc caaacccttc gctgaccgct cggtcgtctc aggccctgag cccacaccct    420
cagcccaccc acttaccttra tgtcagtgag atgctggagg ccaggacagc tgggcacatg    480
cagactctgg ctgacttcag gcagctgcct gcccggactc tctctaccca ctggccaccc    540
caaagatccc tgtgcagctc cgattttatt cgcatccttg tgatcttctc tggaatgttc    600
cttgttttca ccctggccgg ggccctgttc ctccatcaac gaaggaaata tagatcaaac    660
aaaggagaaa gtcctgtgga gcctgcagag ccttgtcgtt acagctgccc cagggaggag    720
gagggcagca ccatccccat ccaggaggat taccgaaaac cggagcctgc ctgctccccc    780
aggagtaaga ggagcaggct cctgcacagt gactacatga acatgactcc ccgccgcccc    840
gggcccaccc gcaagcatta ccagccctat gccccaccac gcgacttcgc agcctatcgc    900
tcccgtttct ctgttgttaa cggggcaga aagaagctcc tgtatatatt caaacaacca    960
tttatgagac cagtacaaac tactcaagag gaagatggct gtagctgccg atttccagaa   1020
gaagaagaag gaggatgtga actgagagtg aagttcagca ggagcgcaga cgcccccgcg   1080
taccagcagg gccagaacca gctctataac gagctcaatc taggacgaag agaggagtac   1140
gatgttttgg acaagagacg tggccgggac cctgagatgg ggggaaagcc gagaaggaag   1200
aaccctcagg aaggcctgta caatgaactg cagaaagata gatggcggaa ggcctacagt   1260
gagattggga tgaaaggcga gcgccggagg ggcaaggggc acgatggcct ttaccagggt   1320
ctcagtacag ccaccaagga cacctacgac gcccttcaca tgcaggccct gcccctcgc   1380
taa                                                                1383
```

<210> SEQ ID NO 21
<211> LENGTH: 188
<212> TYPE: PRT
<213> ORGANISM: Homo sapiens

<400> SEQUENCE: 21

```
Met Ala Arg Pro His Pro Trp Trp Leu Cys Val Leu Gly Thr Leu Val
1               5                   10                  15

Gly Leu Ser Ala Thr Pro Ala Pro Lys Ser Cys Pro Glu Arg His Tyr
            20                  25                  30

Trp Ala Gln Gly Lys Leu Cys Cys Gln Met Cys Glu Pro Gly Thr Phe
        35                  40                  45

Leu Val Lys Asp Cys Asp Gln His Arg Lys Ala Ala Gln Cys Asp Pro
    50                  55                  60

Cys Ile Pro Gly Val Ser Phe Ser Pro Asp His His Thr Arg Pro His
65                  70                  75                  80

Cys Glu Ser Cys Arg His Cys Asn Ser Gly Leu Leu Val Arg Asn Cys
                85                  90                  95

Thr Ile Thr Ala Asn Ala Glu Cys Ala Cys Arg Asn Gly Trp Gln Cys
            100                 105                 110

Arg Asp Lys Glu Cys Thr Glu Cys Asp Pro Leu Pro Asn Pro Ser Leu
        115                 120                 125

Thr Ala Arg Ser Ser Gln Ala Leu Ser Pro His Pro Gln Pro Thr His
    130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
                165                 170                 175
```

His Trp Pro Pro Gln Arg Ser Leu Cys Ser Ser Asp
            180                 185

<210> SEQ ID NO 22
<211> LENGTH: 23
<212> TYPE: PRT
<213> ORGANISM: Homo sapiens

<400> SEQUENCE: 22

Phe Ile Arg Ile Leu Val Ile Phe Ser Gly Met Phe Leu Val Phe Thr
1               5                   10                  15

Leu Ala Gly Ala Leu Phe Leu
            20

<210> SEQ ID NO 23
<211> LENGTH: 49
<212> TYPE: PRT
<213> ORGANISM: Homo sapiens

<400> SEQUENCE: 23

His Gln Arg Arg Lys Tyr Arg Ser Asn Lys Gly Glu Ser Pro Val Glu
1               5                   10                  15

Pro Ala Glu Pro Cys Arg Tyr Ser Cys Pro Arg Glu Glu Glu Gly Ser
            20                  25                  30

Thr Ile Pro Ile Gln Glu Asp Tyr Arg Lys Pro Glu Pro Ala Cys Ser
        35                  40                  45

Pro

<210> SEQ ID NO 24
<211> LENGTH: 1092
<212> TYPE: DNA
<213> ORGANISM: Artificial Sequence
<220> FEATURE:
<223> OTHER INFORMATION: Synthetic

<400> SEQUENCE: 24
atggcatggc cacctcccta ctggctctgc atgctgggga ccttggtagg actctcagct      60
accctagccc caaacagctg tccagacaaa cactactgga ctgggggagg actctgctgc     120
cggatgtgtg agccaggtac attctttgtg aaggactgtg aacaagacag aacagctgct     180
cagtgtgatc cctgtatacc aggcacctcc ttctctccag actaccacac ccggccccac     240
tgcgagagct gcaggcattg taactctggt tttcttatcc gcaactgcac agtcactgcc     300
aatgctgagt gcagctgttc caagaactgg cagtgcaggg accaggaatg tacagagtgt     360
gaccctcctc taaaccctgc actgaccaga cagccatctg agaccccgag cccacagcca     420
ccacccaccc acttacctca tggcacagag aagccatcct ggccccctac aggcagcttt     480
cccaactcga ctgtctatag ccagcggtca tcccatagac ccctgtgcag ctcggactgc     540
atccggatct ttgtgacctt ctccagcatg tttcttatct tcgtcctggg tgcaatcttg     600
ttcttccatc aaagaagaaa ccacgggcca atgaagacc ggcaggcagt gcctgaagag     660
ccttgtcctt acagctgccc cagggaagag gagggcagtg ctatccctat ccaggaggac     720
taccggaaac ccgagcctgc tttctaccct agagcaaaat tcagcaggag tgcagagact     780
gctgccaacc tgcaggaccc caaccagctc tacaatgagc tcaatctagg gcgaagagag     840
gaatatgacg tcttggagaa gaagcgggct cgcgatccag agatggggag caaacagcag     900
aggaggagga accccagga aggcgtatac aatgcactgc agaaagacaa gatggcagaa     960

```
gcctacagtg agatcggcac aaaaggcgag aggcggagag gcaaggggca cgatggcctt   1020
taccagggtc tcagcactgc caccaaggac acctatgatg ccctgcatat gcagaccctg   1080
gcccctcgct aa                                                       1092
```

<210> SEQ ID NO 25
<211> LENGTH: 363
<212> TYPE: PRT
<213> ORGANISM: Artificial Sequence
<220> FEATURE:
<223> OTHER INFORMATION: Synthetic

<400> SEQUENCE: 25

```
Met Ala Trp Pro Pro Tyr Trp Leu Cys Met Leu Gly Thr Leu Val
1               5                   10                  15

Gly Leu Ser Ala Thr Leu Ala Pro Asn Ser Cys Pro Asp Lys His Tyr
            20                  25                  30

Trp Thr Gly Gly Gly Leu Cys Cys Arg Met Cys Glu Pro Gly Thr Phe
        35                  40                  45

Phe Val Lys Asp Cys Glu Gln Asp Arg Thr Ala Ala Gln Cys Asp Pro
    50                  55                  60

Cys Ile Pro Gly Thr Ser Phe Ser Pro Asp Tyr His Thr Arg Pro His
65                  70                  75                  80

Cys Glu Ser Cys Arg His Cys Asn Ser Gly Phe Leu Ile Arg Asn Cys
                85                  90                  95

Thr Val Thr Ala Asn Ala Glu Cys Ser Cys Ser Lys Asn Trp Gln Cys
            100                 105                 110

Arg Asp Gln Glu Cys Thr Glu Cys Asp Pro Pro Leu Asn Pro Ala Leu
        115                 120                 125

Thr Arg Gln Pro Ser Glu Thr Pro Ser Pro Gln Pro Pro Thr His
    130                 135                 140

Leu Pro His Gly Thr Glu Lys Pro Ser Trp Pro Leu His Arg Gln Leu
145                 150                 155                 160

Pro Asn Ser Thr Val Tyr Ser Gln Arg Ser Ser His Arg Pro Leu Cys
                165                 170                 175

Ser Ser Asp Cys Ile Arg Ile Phe Val Thr Phe Ser Ser Met Phe Leu
            180                 185                 190

Ile Phe Val Leu Gly Ala Ile Leu Phe Phe His Gln Arg Arg Asn His
        195                 200                 205

Gly Pro Asn Glu Asp Arg Gln Ala Val Pro Glu Glu Pro Cys Pro Tyr
    210                 215                 220

Ser Cys Pro Arg Glu Glu Gly Ser Ala Ile Pro Ile Gln Glu Asp
225                 230                 235                 240

Tyr Arg Lys Pro Glu Pro Ala Phe Tyr Pro Arg Ala Lys Phe Ser Arg
                245                 250                 255

Ser Ala Glu Thr Ala Ala Asn Leu Gln Asp Pro Asn Gln Leu Tyr Asn
            260                 265                 270

Glu Leu Asn Leu Gly Arg Arg Glu Tyr Asp Val Leu Glu Lys Lys
        275                 280                 285

Arg Ala Arg Asp Pro Glu Met Gly Gly Lys Gln Gln Arg Arg Asn
    290                 295                 300

Pro Gln Glu Gly Val Tyr Asn Ala Leu Gln Lys Asp Lys Met Ala Glu
305                 310                 315                 320

Ala Tyr Ser Glu Ile Gly Thr Lys Gly Glu Arg Arg Gly Lys Gly
                325                 330                 335
```

His Asp Gly Leu Tyr Gln Gly Leu Ser Thr Ala Thr Lys Asp Thr Tyr
            340                 345                 350

Asp Ala Leu His Met Gln Thr Leu Ala Pro Arg
            355                 360

<210> SEQ ID NO 26
<211> LENGTH: 250
<212> TYPE: PRT
<213> ORGANISM: Mus musculus

<400> SEQUENCE: 26

Met Ala Trp Pro Pro Tyr Trp Leu Cys Met Leu Gly Thr Leu Val
1               5                   10                  15

Gly Leu Ser Ala Thr Leu Ala Pro Asn Ser Cys Pro Asp Lys His Tyr
                20                  25                  30

Trp Thr Gly Gly Gly Leu Cys Cys Arg Met Cys Glu Pro Gly Thr Phe
            35                  40                  45

Phe Val Lys Asp Cys Glu Gln Asp Arg Thr Ala Ala Gln Cys Asp Pro
    50                  55                  60

Cys Ile Pro Gly Thr Ser Phe Ser Pro Asp Tyr His Thr Arg Pro His
65                  70                  75                  80

Cys Glu Ser Cys Arg His Cys Asn Ser Gly Phe Leu Ile Arg Asn Cys
                85                  90                  95

Thr Val Thr Ala Asn Ala Glu Cys Ser Cys Ser Lys Asn Trp Gln Cys
                100                 105                 110

Arg Asp Gln Glu Cys Thr Glu Cys Asp Pro Pro Leu Asn Pro Ala Leu
            115                 120                 125

Thr Arg Gln Pro Ser Glu Thr Pro Ser Pro Gln Pro Pro Thr His
    130                 135                 140

Leu Pro His Gly Thr Glu Lys Pro Ser Trp Pro Leu His Arg Gln Leu
145                 150                 155                 160

Pro Asn Ser Thr Val Tyr Ser Gln Arg Ser Ser His Arg Pro Leu Cys
                165                 170                 175

Ser Ser Asp Cys Ile Arg Ile Phe Val Thr Phe Ser Ser Met Phe Leu
            180                 185                 190

Ile Phe Val Leu Gly Ala Ile Leu Phe Phe His Gln Arg Arg Asn His
        195                 200                 205

Gly Pro Asn Glu Asp Arg Gln Ala Val Pro Glu Glu Pro Cys Pro Tyr
    210                 215                 220

Ser Cys Pro Arg Glu Glu Gly Ser Ala Ile Pro Ile Gln Glu Asp
225                 230                 235                 240

Tyr Arg Lys Pro Glu Pro Ala Phe Tyr Pro
            245                 250

<210> SEQ ID NO 27
<211> LENGTH: 113
<212> TYPE: PRT
<213> ORGANISM: Mus musculus

<400> SEQUENCE: 27

Arg Ala Lys Phe Ser Arg Ser Ala Glu Thr Ala Ala Asn Leu Gln Asp
1               5                   10                  15

Pro Asn Gln Leu Tyr Asn Glu Leu Asn Leu Gly Arg Arg Glu Glu Tyr
                20                  25                  30

Asp Val Leu Glu Lys Lys Arg Ala Arg Asp Pro Glu Met Gly Gly Lys
            35                  40                  45

-continued

```
Gln Gln Arg Arg Arg Asn Pro Gln Glu Gly Val Tyr Asn Ala Leu Gln
    50                  55                  60

Lys Asp Lys Met Ala Glu Ala Tyr Ser Glu Ile Gly Thr Lys Gly Glu
65                  70                  75                  80

Arg Arg Arg Gly Lys Gly His Asp Gly Leu Tyr Gln Gly Leu Ser Thr
            85                  90                  95

Ala Thr Lys Asp Thr Tyr Asp Ala Leu His Met Gln Thr Leu Ala Pro
            100                 105                 110

Arg
```

ANTI-CD70 CHIMERIC ANTIGEN RECEPTORS

CROSS-REFERENCE TO RELATED APPLICATIONS

This patent application is a divisional application of copending U.S. patent application Ser. No. 15/531,626, filed May 30, 2017, which is a U.S. national stage of PCT/US2015/025047, filed Apr. 9, 2015, which claims the benefit of U.S. Provisional Patent Application No. 62/088,882, filed Dec. 8, 2014, each of which is incorporated by reference in its entirety herein.

STATEMENT REGARDING FEDERALLY SPONSORED RESEARCH OR DEVELOPMENT

This invention was made with Government support under project number Z01BC011337-04 by the National Institutes of Health, National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: one 55,255 Byte ASCII (Text) file named "749492ST25.TXT," dated Jun. 1, 2020.

BACKGROUND OF THE INVENTION

Cancer is a public health concern. Despite advances in treatments such as chemotherapy, the prognosis for many cancers, including renal cell carcinoma (RCC), glioblastoma, non-Hodgkin's lymphoma (NHL), chronic lymphocytic leukemia (CLL), diffuse large-B-cell lymphoma, and follicular lymphoma, may be poor. Accordingly, there exists an unmet need for additional treatments for cancer, particularly RCC, glioblastoma, NHL, CLL, diffuse large-B-cell lymphoma, and follicular lymphoma.

BRIEF SUMMARY OF THE INVENTION

An embodiment of the invention provides a chimeric antigen receptor (CAR) having antigenic specificity for CD70, the CAR comprising: an antigen binding—transmembrane domain comprising a CD27 amino acid sequence lacking all or a portion of the CD27 intracellular T cell signaling domain, wherein the portion is at least amino acid residues 237 to 260 as defined by SEQ ID NO: 2; a 4-1BB intracellular T cell signaling domain; a CD3ζ intracellular T cell signaling domain; and optionally, a CD28 intracellular T cell signaling domain.

Another embodiment of the invention provides a CAR having antigenic specificity for CD70 comprising an amino acid sequence at least about 90% identical to any one of SEQ ID NOs: 11-13.

Further embodiments of the invention provide related nucleic acids, recombinant expression vectors, host cells, populations of cells, and pharmaceutical compositions relating to the CARs of the invention.

Additional embodiments of the invention provide methods of detecting the presence of cancer in a mammal and methods of treating or preventing cancer in a mammal.

BRIEF DESCRIPTION OF THE SEVERAL VIEWS OF THE DRAWING(S)

FIGS. 1A and 1B are graphs showing the tumor size ($mm^2$) of B16/mCD70- (A) or B16- (B) tumor bearing mice over a period of time (days) following administration of mCD27-CD3ζ CAR-transduced cells (closed circles), untransduced cells (open circles), phosphate buffered saline (PBS) (x), or pmel+VI (squares) and irradiation (500 Rads).

FIGS. 1C and 1D are graphs showing the tumor size ($mm^2$) of B16/mCD70-tumor bearing mice over a period of time (days) following administration of mCD27-CD3ζ CAR-transduced cells at a dose of $1 \times 10^4$ (▼), $1 \times 10^5$ (closed squares), $1 \times 10^6$ (▲), or $1 \times 10^7$ (closed circles) cells per mouse; PBS (open squares); cells transduced with an empty vector (open circles); or pmel+VI (diamonds) with (C) or without (D) irradiation (500 Rads).

FIG. 1E is a graph showing the survival (%) of B16/mCD70-tumor bearing mice over a period of time (days) following administration of mCD27-CD3ζ CAR-transduced cells at a dose of $1 \times 10^4$ (diamonds), $1 \times 10^5$ (▼), $1 \times 10^6$ (▲), or $1 \times 10^7$ (closed circles) cells per mouse; PBS (open squares); cells transduced with an empty vector (open circles); or pmel+VI (Δ), followed by irradiation (500 Rads).

FIGS. 2A-2D are graphs showing the average weight (g) of B16/mCD70- (A and B) or B16- (C and D) tumor bearing mice over a period of time (days) following administration of mCD27-CD3ζ CAR-transduced cells (closed circles), untransduced cells (open squares), phosphate buffered saline (PBS) (∇), or pmel+VI (Δ) with (A and C) or without (B and D) irradiation (500 Rads).

FIGS. 2E-2H are graphs showing the absolute white blood cell count (K/μl) (E and F) or splenocyte count ($\times 10^7$ per spleen) (G and H) of B16/mCD70-tumor bearing mice over a period of time (days) following administration of mCD27-CD3ζ CAR-transduced cells (cross-hatched bars), untransduced cells (unshaded bars), or cells transduced with a vector encoding green fluorescent protein (GFP) (diagonally striped bars) with (E and G) or without (F and H) irradiation (500 Rads).

FIG. 2I is a graph showing serum interferon (IFN) gamma (pg/ml) levels of B16/mCD70-tumor bearing mice over a period of time (days) following administration of mCD27-CD3ζ CAR-transduced cells with (black bars) or without (horizontally striped bars) irradiation or cells transduced with a vector encoding GFP with (checkered bars) or without (unshaded bars) irradiation (500 Rads).

Figure 3:
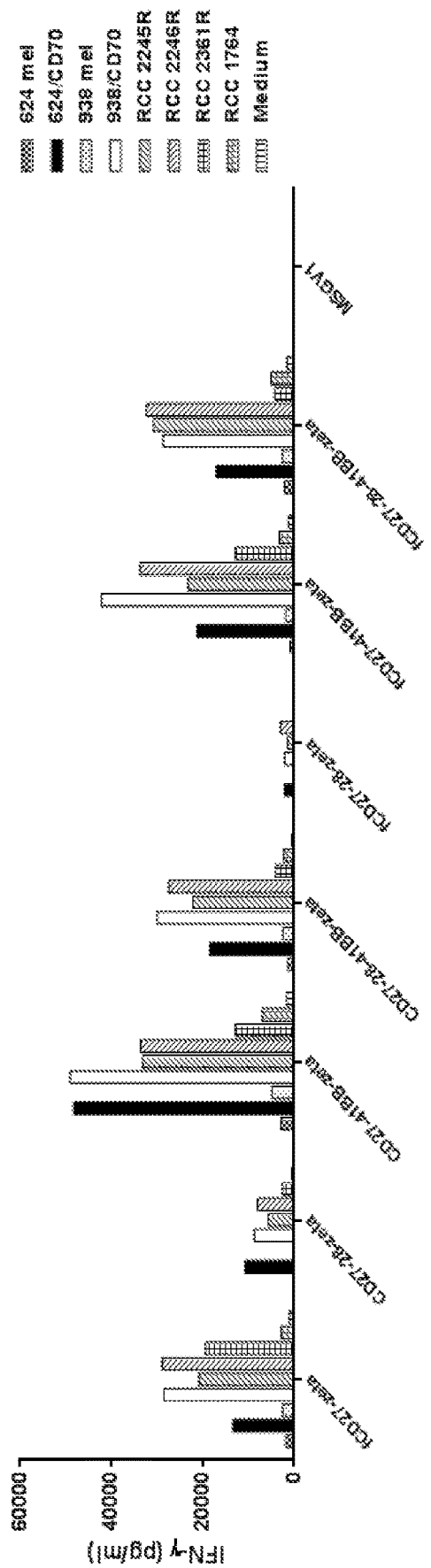

FIG. 3 is a graph showing IFN-γ (pg/ml) secreted upon culture of human T cells transduced with an empty retroviral vector (control) (MSGV1) or one of fCD27-CD3ζ (SEQ ID NO: 7), ΔCD27-CD28—CD3ζ (SEQ ID NO: 8), ΔCD27-4-1BB—CD3ζ (SEQ ID NO: 9), ΔCD27-CD28—4-1BB—CD3ζ (SEQ ID NO: 10), fCD27-CD28—CD3ζ (SEQ ID NO: 11), fCD27-4-1BB—CD3ζ (SEQ ID NO: 12), or fCD27-CD28—4-1BB—CD3ζ (SEQ ID NO: 13) alone (medium) (vertically striped bars) or upon co-culture with control target cells 624mel (checkered bars), 624/CD70 (black bars), 938mel (dotted bars), or 938/CD70 (white bars) or RCC target cells RCC 2245R (forward slashed bars), RCC 2246R (backslashed bars), RCC 2361R (boxed bars), or RCC 1764 (herringbone bars).

Figure 4:
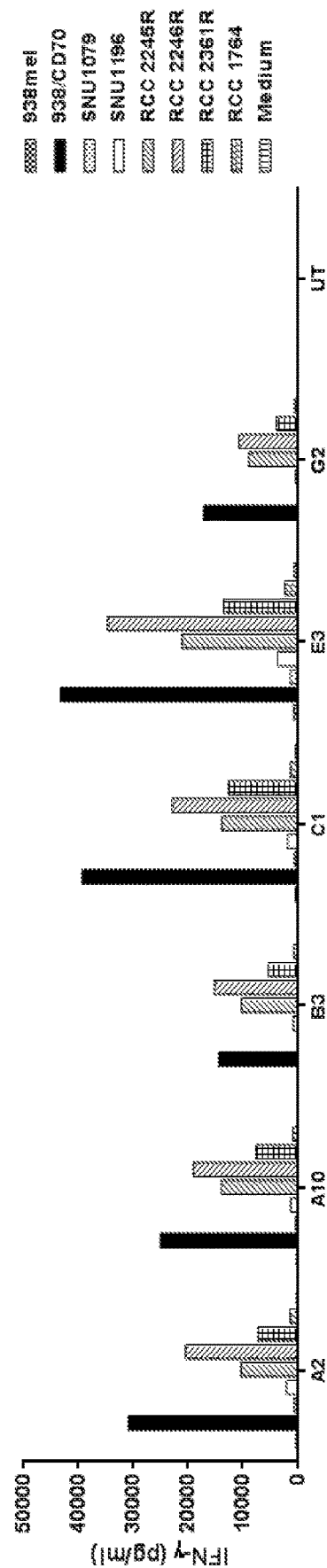

FIG. 4 is a graph showing IFN-γ (pg/ml) secreted upon culture of untransduced (UT) cells or retroviral packaging clone A2, A10, B3, C1, E3, or G2 transduced with ΔCD27-4-1BB—CD3ζ (SEQ ID NO: 9) alone (medium, vertically striped bars) or upon co-culture with control target cells SNU1079 (dotted bars), SNU1196 (white bars), 938mel (checkered bars), or 938/CD70 (black bars) or RCC target cells RCC 2245R (forward slashed bars), RCC 2246R (backslashed bars), RCC 2361R (boxed bars), or RCC 1764 (herringbone bars).

Figure 5:
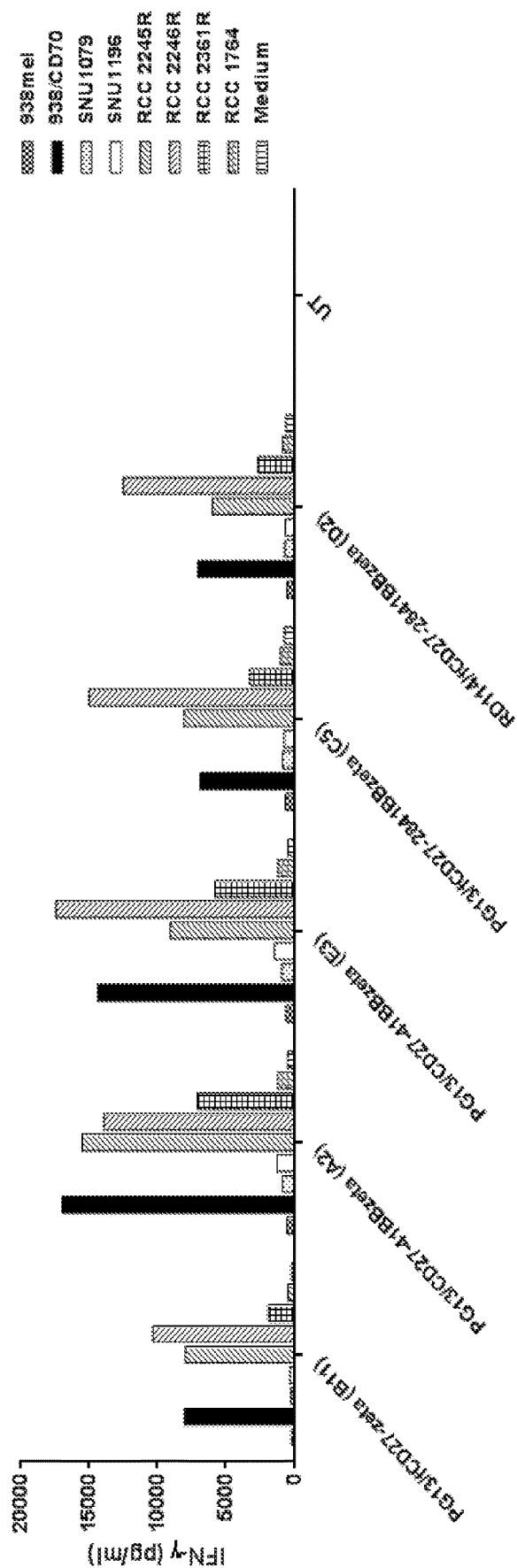

FIG. 5 is a graph showing IFN-γ (pg/ml) secreted upon culture of untransduced (UT) cells or retroviral packaging clone A2, B11, C5, or D2 transduced with ΔCD27-4-1BB—CD3ζ (SEQ ID NO: 9) alone (medium, vertically striped bars) or upon co-culture with control target cells SNU1079 (dotted bars), SNU1196 (white bars), 938mel (checkered bars), or 938/CD70 (black bars) or RCC target cells RCC 2245R (forward slashed bars), RCC 2246R (backslashed bars), RCC 2361R (boxed bars), or RCC 1764 (herringbone bars).

DETAILED DESCRIPTION OF THE INVENTION

An embodiment of the invention provides a chimeric antigen receptor (CAR) having antigenic specificity for CD70, the CAR comprising: an antigen binding—transmembrane domain comprising a CD27 amino acid sequence lacking all or a portion of the CD27 intracellular T cell signaling domain, wherein the portion is at least amino acid residues 237 to 260 as defined by SEQ ID NO: 2; a 4-1BB intracellular T cell signaling domain; a CD3ζ intracellular T cell signaling domain; and optionally, a CD28 intracellular T cell signaling domain. Hereinafter, references to a "CAR" also refer to functional portions and functional variants of the CAR, unless specified otherwise.

A CAR is an artificially constructed hybrid protein or polypeptide containing the antigen binding domains of a receptor (e.g., a tumor necrosis factor (TNF) receptor) linked to T-cell signaling domains. Characteristics of CARs include their ability to redirect T-cell specificity and reactivity toward a selected target in a non-major histocompatibility complex (MHC)-restricted manner, exploiting the antigen-binding properties of receptors. The non-MHC-restricted antigen recognition gives T cells expressing CARs the ability to recognize antigen independent of antigen processing, thus bypassing a major mechanism of tumor escape. Moreover, when expressed in T-cells, CARs advantageously do not dimerize with endogenous T cell receptor (TCR) alpha and beta chains.

The phrases "have antigen(ic) specificity" and "elicit antigen-specific response," as used herein, means that the CAR can specifically bind to and immunologically recognize an antigen, such that binding of the CAR to the antigen elicits an immune response.

The CARs of the invention have antigen specificity for CD70. CD70 belongs to the TNF superfamily and has the amino acid sequence of SEQ ID NO: 1 CD70 is a co-stimulatory molecule that is involved in the proliferation and survival of lymphoid-derived cells when it interacts with its receptor, CD27. Normal, non-cancerous expression of CD70 is restricted to lymphoid tissues such as activated T cells, B cells, natural killer (NK) cells, monocytes, and dendritic cells. CD70 is expressed in a variety of human cancers such as, for example, RCC (Diegmann et al., *Eur. J Cancer*, 41: 1794-801 (2005)) (for example, clear cell RCC (ccRCC)), glioblastoma (Held-Feindt et al. *Int. J. Cancer*, 98: 352-56 (2002); Wischhusen et al., *Cancer Res.*, 62: 2592-99 (2002)), NHL and CLL (Lens et al., *Br. J Haematol.*, 106: 491-503 (1999)), diffuse large-B-cell lymphoma, and follicular lymphoma.

Without being bound to a particular theory or mechanism, it is believed that by eliciting an antigen-specific response against CD70, the inventive CARs provide for one or more of any of the following: targeting and destroying CD70-expressing cancer cells, reducing or eliminating cancer cells, facilitating infiltration of immune cells to tumor site(s), and enhancing/extending anti-cancer responses. Because normal CD70 expression is limited to lymphoid tissues such as activated T cells, B cells, NK cells, monocytes, and dendritic cells, it is contemplated that the inventive CARs advantageously substantially avoid targeting/destroying many normal tissues.

An embodiment of the invention provides a CAR comprising an antigen binding—transmembrane domain comprising a CD27 amino acid sequence. In this regard, the CAR may comprise both a CD27 antigen binding domain and a CD27 transmembrane domain. The CD27 may comprise or consist of any suitable human antigen binding—transmembrane domain CD27 amino acid sequence. In an embodiment of the invention, full-length CD27, including the antigen binding domain, the transmembrane domain, and the intracellular T cell signaling domain, has the amino acid sequence of SEQ ID NO: 2. In an embodiment of the invention, the antigen binding domain of CD27 is composed of amino acid residues 1-188 of SEQ ID NO: 2 and has the amino acid sequence of SEQ ID NO: 21, the transmembrane domain of CD27 is composed of amino acid residues 189-211 of SEQ ID NO: 2 and has the amino acid sequence of SEQ ID NO: 22, and the intracellular T cell signaling domain of CD27 is composed of amino acid residues 212-260 of SEQ ID NO: 2 and has the amino acid sequence of SEQ ID NO: 23. Accordingly, in an embodiment of the invention, the CAR comprises an antigen binding—transmembrane domain comprising the amino acid sequences of SEQ ID NOs: 21 and 22. The antigen binding domain of CD27 specifically binds to CD70.

An embodiment of the invention provides a CAR comprising an antigen binding—transmembrane domain comprising a CD27 amino acid sequence lacking all or a portion of the CD27 intracellular T cell signaling domain, wherein the portion that is lacking from the CAR is at least contiguous amino acid residues 237 to 260, at least contiguous amino acid residues 236 to 260, at least contiguous amino acid residues 235 to 260, at least contiguous amino acid residues 234 to 260, at least contiguous amino acid residues 233 to 260, at least contiguous amino acid residues 232 to 260, at least contiguous amino acid residues 231 to 260, at least contiguous amino acid residues 230 to 260, at least contiguous amino acid residues 229 to 260, at least contiguous amino acid residues 228 to 260, at least contiguous amino acid residues 227 to 260, at least contiguous amino acid residues 226 to 260, at least contiguous amino acid residues 225 to 260, at least contiguous amino acid residues 224 to 260, at least contiguous amino acid residues 223 to 260, at least contiguous amino acid residues 222 to 260, at least contiguous amino acid residues 221 to 260, at least contiguous amino acid residues 220 to 260, at least contiguous amino acid residues 219 to 260, at least contiguous amino acid residues 218 to 260, at least contiguous amino acid residues 217 to 260, at least contiguous amino acid residues 216 to 260, at least contiguous amino acid residues 215 to 260, at least contiguous amino acid residues 214 to 260, or at least contiguous amino acid residues 213 to 260, as defined by SEQ ID NO: 2. In an embodiment of the invention, the antigen binding—transmembrane domain comprises a CD27 amino acid sequence lacking contiguous amino acid residues 237 to 260, contiguous amino acid residues 236 to 260, contiguous amino acid residues 235 to 260, contiguous amino acid residues 234 to 260, contiguous amino acid residues 233 to 260, contiguous amino acid residues 232 to 260, contiguous amino acid residues 231 to 260, contiguous amino acid residues 230 to 260, contiguous amino acid residues 229 to 260, contiguous amino acid residues 228 to 260, contiguous amino acid residues 227 to 260, contiguous amino acid residues 226 to 260, contiguous amino acid residues 225 to 260, contiguous amino acid residues 224 to 260, contiguous amino acid residues 223 to 260, contiguous amino acid residues 222 to 260, contiguous amino acid residues 221 to 260, contiguous amino acid residues 220 to 260, contiguous amino acid residues 219 to 260, contiguous amino acid residues 218 to 260, contiguous amino acid residues 217 to 260, contiguous amino acid residues 216 to 260, contiguous amino acid residues 215 to 260, contiguous amino acid residues 214 to 260, or contiguous amino acid residues 213 to 260, of SEQ ID NO: 2. A CD27 amino acid sequence lacking all or a portion of the CD27 intracellular T cell signaling domain is also referred to herein as a "truncated CD27 amino acid sequence" or a "truncated CD27."

In a preferred embodiment, the antigen binding—transmembrane domain comprises a CD27 amino acid sequence lacking all of the CD27 intracellular T cell signaling domain. In this regard, the antigen binding—transmembrane domain comprises a CD27 amino acid sequence lacking contiguous amino acid residues 212 to 260 as defined by SEQ ID NO: 2 or a CD27 amino acid sequence lacking contiguous amino acid residues 212 to 260 of SEQ ID NO: 2. In an embodiment of the invention, the antigen binding—transmembrane domain comprises a CD27 amino acid sequence lacking the amino acid sequence of SEQ ID NO: 23. In an embodiment of the invention, the antigen binding—transmembrane domain that comprises a CD27 amino acid sequence lacking all of the CD27 intracellular T cell signaling domain comprises or consists of an amino acid sequence at least about 90%, about 91%, about 92%, about 93%, about 94%, about 95%, about 96%, about 97%, about 98%, or about 99% identical to SEQ ID NO: 3 or which comprises or consists of the amino acid sequence of SEQ ID NO: 3.

The CAR may further comprise a 4-1BB intracellular T cell signaling domain; a CD3 zeta (ζ) intracellular T cell signaling domain; and optionally, a CD28 intracellular T cell signaling domain. In an embodiment of the invention, the CAR comprises comprising a 4-1BB intracellular T cell signaling domain, a CD3ζ intracellular T cell signaling domain, and a CD28 intracellular T cell signaling domain. In another embodiment of the invention, the CAR comprises a 4-1BB intracellular T cell signaling domain and a CD3ζ intracellular T cell signaling domain. In a preferred embodiment, the 4-1BB, CD3ζ, and CD28 intracellular T cell signaling domains are human. CD28 is a T cell marker important in T cell co-stimulation. 4-1BB, also known as CD137, transmits a potent costimulatory signal to T cells, promoting differentiation and enhancing long-term survival of T lymphocytes. CD3ζ associates with TCRs to produce a signal and contains immunoreceptor tyrosine-based activation motifs (ITAMs).

The CD3ζ intracellular T cell signaling domain may comprise or consist of any suitable human CD3ζ intracellular T cell signaling domain amino acid sequence. In an embodiment of the invention, the CD3ζ intracellular T cell signaling domain comprises or consists of an amino acid sequence at least about 90%, about 91%, about 92%, about 93%, about 94%, about 95%, about 96%, about 97%, about 98%, or about 99% identical to SEQ ID NO: 4. Preferably, the CD3ζ intracellular T cell signaling domain comprises or consists of the amino acid sequence of SEQ ID NO: 4.

The 4-1BB intracellular T cell signaling domain may comprise or consist of any suitable human 4-1BB intracellular T cell signaling domain amino acid sequence. In an embodiment of the invention, the 4-1BB intracellular T cell signaling domain comprises or consists of an amino acid sequence at least about 90%, about 91%, about 92%, about 93%, about 94%, about 95%, about 96%, about 97%, about 98%, or about 99% identical to SEQ ID NO: 5. Preferably, the 4-1BB intracellular T cell signaling domain comprises or consists of the amino acid sequence of SEQ ID NO: 5.

The CD28 intracellular T cell signaling domain may comprise or consist of any suitable human CD28 intracellular T cell signaling domain amino acid sequence. In an embodiment of the invention, the CD28 intracellular T cell signaling domain comprises or consists of an amino acid sequence at least about 90%, about 91%, about 92%, about 93%, about 94%, about 95%, about 96%, about 97%, about 98%, or about 99% identical to SEQ ID NO: 6. Preferably, the CD28 intracellular T cell signaling domain comprises or consists of the amino acid sequence of SEQ ID NO: 6.

In an embodiment of the invention, the CAR comprises a full-length CD27 amino acid sequence, including a CD27 antigen binding domain, a CD27 transmembrane domain, and a CD27 intracellular T cell signaling domain, in combination with a CD3ζ intracellular T cell signaling domain (full length (f)CD27-CD3ζ CAR). In this regard, the CAR may comprise or consist of a full-length CD27 amino acid sequence at least about 90%, about 91%, about 92%, about 93%, about 94%, about 95%, about 96%, about 97%, about 98%, or about 99% identical to SEQ ID NO: 2 and any of the CD3ζ amino acid sequences described herein with respect to other aspects of the invention. For example, the fCD27-CD3ζ CAR may comprise or consist of the full-length CD27 amino acid sequence of SEQ ID NO: 2 and the CD3ζ amino acid sequence of SEQ ID NO: 4. In an embodiment of the invention, the fCD27-CD3ζ CAR may comprise or consist of an amino acid sequence at least about 90%, about 91%, about 92%, about 93%, about 94%, about 95%, about 96%, about 97%, about 98%, or about 99% identical to SEQ ID NO: 7. Preferably, the fCD27-CD3ζ CAR comprises or consists of the amino acid sequence of SEQ ID NO: 7. In an embodiment of the invention, the fCD27-CD3ζ CAR lacks one or both of truncated CD19 and DsRed.

In an embodiment of the invention, the CAR comprises a full-length CD27 amino acid sequence, including a CD27 antigen binding domain, a CD27 transmembrane domain, and a CD27 intracellular T cell signaling domain, in combination with a CD3ζ intracellular T cell signaling domain and a CD28 intracellular T cell signaling domain (fCD27-CD28-CD3ζ). In this regard, the CAR may comprise or consist of any of the full-length CD27 amino acid sequences, any of the CD3ζ amino acid sequences, and any of the CD28 amino acid sequences described herein with respect to other aspects of the invention. For example, the fCD27-CD28-CD3ζ CAR may comprise or consist of the full-length CD27 amino acid sequence of SEQ ID NO: 2, the CD3ζ amino acid sequence of SEQ ID NO: 4, and the CD28 amino acid sequence of SEQ ID NO: 6. In an embodiment of the invention, the fCD27-CD28-CD3ζ CAR may comprise or consist of an amino acid sequence at least about 90%, about 91%, about 92%, about 93%, about 94%, about 95%, about 96%, about 97%, about 98%, or about 99% identical to SEQ ID NO: 11. Preferably, the fCD27-CD28-CD3ζ CAR comprises or consists of the amino acid sequence of SEQ ID NO: 11.

In an embodiment of the invention, the CAR comprises a full-length CD27 amino acid sequence, including a CD27 antigen binding domain, a CD27 transmembrane domain, and a CD27 intracellular T cell signaling domain, in combination with a CD3ζ intracellular T cell signaling domain and a 4-1BB intracellular T cell signaling domain (fCD27-4-1BB-CD3ζ). In this regard, the CAR may comprise or consist of any of the full-length CD27 amino acid sequences, any of the CD3ζ amino acid sequences, and any of the 4-1BB amino acid sequences described herein with respect to other aspects of the invention. For example, the fCD27-4-1BB-CD3ζ CAR may comprise or consist of the full-length CD27 amino acid sequence of SEQ ID NO: 2, the CD3ζ amino acid sequence of SEQ ID NO: 4, and the 4-1BB amino acid sequence of SEQ ID NO: 5. In an embodiment of the invention, the fCD27-4-1BB-CD3ζ CAR may comprise or consist of an amino acid sequence at least about 90%, about 91%, about 92%, about 93%, about 94%, about 95%, about 96%, about 97%, about 98%, or about 99% identical to SEQ ID NO: 12. Preferably, the fCD27-4-1BB-CD3ζ CAR comprises or consists of the amino acid sequence of SEQ ID NO: 12.

In an embodiment of the invention, the CAR comprises a full-length CD27 amino acid sequence, including a CD27 antigen binding domain, a CD27 transmembrane domain, and a CD27 intracellular T cell signaling domain, in combination with a CD3ζ intracellular T cell signaling domain, a 4-1BB intracellular T cell signaling domain, and a CD28 intracellular signaling domain (fCD27-CD28-4-1BB-CD3ζ). In this regard, the CAR may comprise or consist of any of the full-length CD27 amino acid sequences, any of the CD3ζ amino acid sequences, any of the 4-1BB amino acid sequences, and any of the CD28 amino acid sequences described herein with respect to other aspects of the invention. For example, the fCD27-CD28-4-1BB-CD3ζ CAR may comprise or consist of the full-length CD27 amino acid sequence of SEQ ID NO: 2, the CD3ζ amino acid sequence of SEQ ID NO: 4, the 4-1BB amino acid sequence of SEQ ID NO: 5, and the CD28 amino acid sequence of SEQ ID NO: 6. In an embodiment of the invention, the fCD27-CD28-4-1BB-CD3ζ CAR may comprise or consist of an amino acid sequence at least about 90%, about 91%, about 92%, about 93%, about 94%, about 95%, about 96%, about 97%, about 98%, or about 99% identical to SEQ ID NO: 13. Preferably, the fCD27-CD28-4-1BB-CD3ζ CAR comprises or consists of the amino acid sequence of SEQ ID NO: 13.

In an embodiment of the invention, the CAR comprises a full-length mouse CD27 amino acid sequence, including a CD27 antigen binding domain, a CD27 transmembrane domain, and a CD27 intracellular T cell signaling domain, in combination with a mouse CD3ζ intracellular T cell signaling domain (mCD27-CD3ζ). In this regard, the CAR may comprise or consist of a full-length mouse CD27 amino acid sequence at least about 90%, about 91%, about 92%, about 93%, about 94%, about 95%, about 96%, about 97%, about 98%, or about 99% identical to SEQ ID NO: 26 in combination with a mouse CD3ζ amino acid sequence at least about 90%, about 91%, about 92%, about 93%, about 94%, about 95%, about 96%, about 97%, about 98%, or about 99% identical to SEQ ID NO: 27. For example, the mCD27-CD3ζ CAR may comprise or consist of the full-length mouse CD27 amino acid sequence of SEQ ID NO: 26 and the mouse CD3ζ amino acid sequence of SEQ ID NO: 27. In an embodiment of the invention, the mCD27-CD3ζ CAR may comprise or consist of an amino acid sequence at least about 90%, about 91%, about 92%, about 93%, about 94%, about 95%, about 96%, about 97%, about 98%, or about 99% identical to SEQ ID NO: 25. Preferably, the mCD27-CD3ζ CAR comprises or consists of the amino acid sequence of SEQ ID NO: 25.

In an embodiment of the invention, the CAR comprises an antigen binding—transmembrane domain comprising a truncated CD27 amino acid sequence which lacks all of the CD27 intracellular T cell signaling domain, in combination with a CD3ζ intracellular T cell signaling domain and a CD28 intracellular T cell signaling domain (truncated (Δ) CD27-CD28—CD3ζ). In this regard, the CAR may comprise or consist of a truncated CD27 antigen binding—transmembrane domain amino acid sequence at least about 90%, about 91%, about 92%, about 93%, about 94%, about 95%, about 96%, about 97%, about 98%, or about 99% identical to SEQ ID NO: 3 in combination with any of the CD3ζ intracellular T cell signaling domain amino acid sequences and any of the CD28 intracellular T cell signaling domain amino acid sequences described herein with respect to other aspects of the invention. For example, the ΔCD27-CD28—CD3ζ CAR may comprise or consist of the truncated CD27 antigen binding—transmembrane domain amino acid sequence of SEQ ID NO: 3, the CD3ζ amino acid sequence of SEQ ID NO: 4, and the CD28 amino acid sequence of SEQ ID NO: 6. In an embodiment of the invention, the ΔCD27-CD28—CD3ζ CAR may comprise or consist of an amino acid sequence at least about 90%, about 91%, about 92%, about 93%, about 94%, about 95%, about 96%, about 97%, about 98%, or about 99% identical to SEQ ID NO: 8. Preferably, the ΔCD27-CD28—CD3ζ CAR comprises or consists of the amino acid sequence of SEQ ID NO: 8.

In an embodiment of the invention, the CAR comprises an antigen binding—transmembrane domain comprising a truncated CD27 amino acid sequence which lacks all of the CD27 intracellular T cell signaling domain, in combination with a CD3ζ intracellular T cell signaling domain and a 4-1BB intracellular T cell signaling domain (ΔCD27-4-1BB—CD3ζ). In this regard, the CAR may comprise or consist of any of the truncated CD27 antigen binding—transmembrane domain amino acid sequences, any of the CD3ζ intracellular T cell signaling domain amino acid sequences, and any of the 4-1BB intracellular T cell signaling domain amino acid sequences described herein with respect to other aspects of the invention. For example, the ΔCD27-4-1BB—CD3ζ CAR may comprise or consist of the truncated CD27 antigen binding—transmembrane domain amino acid sequence of SEQ ID NO: 3, the CD3ζ amino acid sequence of SEQ ID NO: 4, and the 4-1BB amino acid sequence of SEQ ID NO: 5. In an embodiment of the invention, the ΔCD27-4-1BB—CD3ζ CAR may comprise or consist of an amino acid sequence at least about 90%, about 91%, about 92%, about 93%, about 94%, about 95%, about 96%, about 97%, about 98%, or about 99% identical to SEQ ID NO: 9. Preferably, the ΔCD27-4-1BB—CD3ζ CAR comprises or consists of the amino acid sequence of SEQ ID NO: 9.

In an embodiment of the invention, the CAR comprises an antigen binding—transmembrane domain comprising a truncated CD27 amino acid sequence which lacks all of the CD27 intracellular T cell signaling domain, in combination with a CD3ζ intracellular T cell signaling domain, a CD28 intracellular T cell signaling domain, and a 4-1BB intracellular T cell signaling domain (ΔCD27-CD28—4-1BB—CD3ζ). In this regard, the CAR may comprise or consist of any of the truncated CD27 antigen binding—transmembrane domain amino acid sequences, any of the CD3ζ intracellular T cell signaling domain amino acid sequences, any of the CD28 intracellular T cell signaling domain amino acid sequences, and any of the 4-1BB intracellular T cell signaling domain amino acid sequences described herein with respect to other aspects of the invention. For example, the ΔCD27-CD28—4-1BB—CD3ζ CAR may comprise or consist of the truncated CD27 antigen binding—transmembrane domain amino acid sequence of SEQ ID NO: 3, the CD3ζ amino acid sequence of SEQ ID NO: 4, the CD28 amino acid sequence of SEQ ID NO: 6, and the 4-1BB amino acid sequence of SEQ ID NO: 5. In an embodiment of the invention, the ΔCD27-CD28—4-1BB—CD3ζ CAR may comprise or consist of an amino acid sequence at least about 90%, about 91%, about 92%, about 93%, about 94%, about 95%, about 96%, about 97%, about 98%, or about 99% identical to SEQ ID NO: 10. Preferably, the ΔCD27-CD28 4-1BB—CD3ζ CAR comprises or consists of the amino acid sequence of SEQ ID NO: 10.

In an embodiment of the invention, the CAR comprises an amino acid sequence at least about 90% identical to any one of SEQ ID NOs: 8-10. In an embodiment of the invention, the CAR comprises an amino acid sequence at least about 90% identical to SEQ ID NO: 9 or 10. In another embodiment of the invention, the CAR comprises an amino acid sequence at least about 90% identical to any one of SEQ ID NOs: 11-13. In another embodiment of the invention, the CAR comprises an amino acid sequence at least about 90% identical to SEQ ID NO: 12 or 13. Preferably, the CAR comprises, consists of, or consists essentially of any one of the amino acid sequences set forth in Table 1A. In a preferred embodiment of the invention, the CAR comprises the amino acid sequence of any one of SEQ ID NOs: 7-13. Preferably, the CAR comprises the amino acid sequence of any one of SEQ ID NO: 9, 10, 12, and 13.

TABLE 1A

| CAR | Antigen binding and Transmembrane Domain | Intracellular T Cell Signaling Domain |
| --- | --- | --- |
| full length (f) CD27-CD3ζ (SEQ ID NO: 7) | full length human CD27 | human CD27 and human CD3ζ |
| truncated (Δ) CD27-CD28 - CD3ζ (SEQ ID NO: 8) | truncated human CD27 | human CD28 and human CD3ζ |
| ΔCD27-4-1BB - CD3ζ (SEQ ID NO: 9) | truncated human CD27 | human 4-1BB and human CD3ζ |
| ΔCD27-CD28 - 4-1BB - CD3ζ (SEQ ID NO: 10) | truncated human CD27 | human 4-1BB human CD28 and human CD3ζ |
| fCD27-CD28 - CD3ζ (SEQ ID NO: 11) | full-length human CD27 | human CD27 human CD28 and human CD3ζ |
| fCD27-4-1BB - CD3ζ (SEQ ID NO: 12) | full-length human CD27 | human CD27 human 4-1BB and human CD3ζ |
| fCD27-CD28 - 4-1BB - CD3ζ (SEQ ID NO: 13) | full-length human CD27 | human CD27 human 4-1BB human CD28 and human CD3ζ |
| mCD27-CD3ζ (SEQ ID NO: 25) | full length mouse CD27 | mouse CD3ζ |

Included in the scope of the invention are functional portions of the inventive CARs described herein. The term "functional portion" when used in reference to a CAR refers to any part or fragment of the CAR of the invention, which part or fragment retains the biological activity of the CAR of which it is a part (the parent CAR). Functional portions encompass, for example, those parts of a CAR that retain the ability to recognize target cells, or detect, treat, or prevent cancer, to a similar extent, the same extent, or to a higher extent, as the parent CAR. In reference to the parent CAR, the functional portion can comprise, for instance, about 10%, about 25%, about 30%, about 50%, about 68%, about 80%, about 90%, about 95%, or more, of the parent CAR.

The functional portion can comprise additional amino acids at the amino or carboxy terminus of the portion, or at both termini, which additional amino acids are not found in the amino acid sequence of the parent CAR. Desirably, the additional amino acids do not interfere with the biological function of the functional portion, e.g., recognize target cells, detect cancer, treat or prevent cancer, etc. More desirably, the additional amino acids enhance the biological activity, as compared to the biological activity of the parent CAR.

Included in the scope of the invention are functional variants of the inventive CARs described herein. The term "functional variant" as used herein refers to a CAR, polypeptide, or protein having substantial or significant sequence identity or similarity to a parent CAR, which functional variant retains the biological activity of the CAR of which it is a variant. Functional variants encompass, for example, those variants of the CAR described herein (the parent CAR) that retain the ability to recognize target cells to a similar extent, the same extent, or to a higher extent, as the parent CAR. In reference to the parent CAR, the functional variant can, for instance, be at least about 30%, about 50%, about 75%, about 80%, about 90%, about 91%, about 92%, about 93%, about 94%, about 95%, about 96%, about 97%, about 98%, about 99% or more identical in amino acid sequence to the parent CAR.

A functional variant can, for example, comprise the amino acid sequence of the parent CAR with at least one conservative amino acid substitution. Alternatively or additionally, the functional variants can comprise the amino acid sequence of the parent CAR with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent CAR.

Amino acid substitutions of the inventive CARs are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gln, Ser, Thr, Tyr, etc.), an amino acid with a beta-branched side-chain substituted for another amino acid with a beta-branched side-chain (e.g., Ile, Thr, and Val), an amino acid with an aromatic side-chain substituted for another amino acid with an aromatic side chain (e.g., His, Phe, Trp, and Tyr), etc.

The CAR can consist essentially of the specified amino acid sequence or sequences described herein, such that other components, e.g., other amino acids, do not materially change the biological activity of the functional variant.

The CARs of embodiments of the invention can be of any length, i.e., can comprise any number of amino acids, provided that the CARs retain their biological activity, e.g., the ability to specifically bind to antigen, detect cancer cells in a mammal, or treat or prevent cancer in a mammal, etc. For example, the CAR can be about 50 to about 5000 amino acids long, such as 50, 70, 75, 100, 125, 150, 175, 200, 300, 400, 500, 600, 700, 800, 900, 1000 or more amino acids in length.

The CARs of embodiments of the invention can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbomane)-carboxylic acid, α,γ-diaminobutyric acid, α,β-diaminopropionic acid, homophenylalanine, and α-tert-butylglycine.

The CARs of embodiments of the invention can be glycosylated, amidated, carboxylated, phosphorylated, esterified, N-acylated, cyclized via, e.g., a disulfide bridge, or converted into an acid addition salt and/or optionally dimerized or polymerized, or conjugated.

The CARs of embodiments of the invention can be obtained by methods known in the art such as, for example, de novo synthesis. Also, polypeptides and proteins can be recombinantly produced using the nucleic acids described herein using standard recombinant methods. See, for instance, Green and Sambrook, *Molecular Cloning: A Laboratory Manual*, 4$^{th}$ ed., Cold Spring Harbor Press, Cold Spring Harbor, NY (2012). Alternatively, the CARs described herein can be commercially synthesized by companies, such as Synpep (Dublin, CA), Peptide Technologies Corp. (Gaithersburg, MD.), and Multiple Peptide Systems (San Diego, CA). In this respect, the inventive CARs can be synthetic, recombinant, isolated, and/or purified.

Further provided by an embodiment of the invention is a nucleic acid comprising a nucleotide sequence encoding any of the CARs described herein. The nucleic acids of the invention may comprise a nucleotide sequence encoding any of the antigen binding domains, transmembrane domains, and/or intracellular T cell signaling domains described herein. In an embodiment of the invention, the nucleic acid comprises, consists of, or consists essentially of any one of the nucleotide sequences set forth in Table 1B. Preferably, the nucleic acid comprises the nucleotide sequence of any one of SEQ ID NOs: 14-20. Preferably, the nucleic acid comprises the nucleotide sequence of any one of SEQ ID NOs: 16, 17, 19, and 20. In an embodiment of the invention, the nucleotide sequence encoding the fCD27-CD3ζ CAR does not encode one or both of truncated CD19 and DsRed.

TABLE 1B

| CAR | Antigen binding and Transmembrane Domain | Intracellular T Cell Signaling Domain |
| --- | --- | --- |
| full length (f) CD27-CD3ζ (SEQ ID NO: 14) | full length human CD27 | human CD27 and human CD3ζ |
| truncated (Δ) CD27-CD28 - CD3ζ (SEQ ID NO: 15) | truncated human CD27 | human CD28 and human CD3ζ |
| ΔCD27-4-1BB - CD3ζ (SEQ ID NO: 16) | truncated human CD27 | human 4-1BB and human CD3ζ |
| ΔCD27-CD28 - 4-1BB - CD3ζ (SEQ ID NO: 17) | truncated human CD27 | human 4-1BB human CD28 and human CD3ζ |
| fCD27-CD28 - CD3ζ (SEQ ID NO: 18) | full-length human CD27 | human CD27 human CD28 and human CD3ζ |
| fCD27-4-1BB - CD3ζ (SEQ ID NO: 19) | full-length human CD27 | human CD27 human 4-1BB and human CD3ζ |
| fCD27-CD28 - 4-1BB - CD3ζ (SEQ ID NO: 20) | full-length human CD27 | human CD27 human 4-1BB human CD28 and human CD3ζ |
| mCD27-CD3ζ (SEQ ID NO: 24) | full length mouse CD27 | mouse CD3ζ |

"Nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions. In some embodiments, the nucleic acid may encode additional amino acid sequences that do not affect the function of the CAR and which may or may not be translated upon expression of the nucleic acid by a host cell.

The nucleic acids of an embodiment of the invention may be recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

A recombinant nucleic acid may be one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques, such as those described in Green and Sambrook, supra. The nucleic acids can be constructed based on chemical synthesis and/or enzymatic ligation reactions using procedures known in the art. See, for example, Green and Sambrook, supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxy acetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, CO) and Synthegen (Houston, TX).

The nucleic acid can comprise any isolated or purified nucleotide sequence which encodes any of the CARs described herein with respect to other aspects of the invention. Alternatively, the nucleotide sequence can comprise a nucleotide sequence which is degenerate to any of the sequences or a combination of degenerate sequences.

An embodiment of the invention also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions may hybridize under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive CARs. It is generally appreciated that conditions can be rendered more stringent by the addition of increasing amounts of formamide.

The invention also provides a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein.

In an embodiment, the nucleic acids of the invention can be incorporated into a recombinant expression vector. In this regard, an embodiment of the invention provides recombinant expression vectors comprising any of the nucleic acids of the invention. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the non-naturally occurring or altered nucleotides or internucleotide linkages do not hinder the transcription or replication of the vector. In an embodiment of the invention, the recombinant expression vector comprising the nucleotide sequence encoding the fCD27-CD3ζ CAR does not encode one or both of truncated CD19 and DsRed.

In an embodiment, the recombinant expression vector of the invention can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences, Glen Burnie, MD), the pBluescript series (Stratagene, LaJolla, CA), the pET series (Novagen, Madison, WI), the pGEX series (Pharmacia Biotech, Uppsala, Sweden), and the pEX series (Clontech, Palo Alto, CA). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM, and pMAMneo (Clontech). The recombinant expression vector may be a viral vector, e.g., a retroviral vector or a lentiviral vector. In some embodiments, the vector can be a transposon.

In an embodiment, the recombinant expression vectors of the invention can be prepared using standard recombinant DNA techniques described in, for example, Green and Sambrook, supra. Constructs of expression vectors, which are circular or linear, can be prepared to contain a replication system functional in a prokaryotic or eukaryotic host cell. Replication systems can be derived, e.g., from ColE1, 2μ plasmid, λ, SV40, bovine papilloma virus, and the like.

The recombinant expression vector may comprise regulatory sequences, such as transcription and translation initiation and termination codons, which are specific to the type of host cell (e.g., bacterium, fungus, plant, or animal) into which the vector is to be introduced, as appropriate, and taking into consideration whether the vector is DNA- or RNA-based. The recombinant expression vector may comprise restriction sites to facilitate cloning.

The recombinant expression vector can include one or more marker genes, which allow for selection of transformed or transfected host cells. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the CAR, or to the nucleotide sequence which is complementary to or which hybridizes to the nucleotide sequence encoding the CAR. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art and include, for example, the Herpes Simplex Virus (HSV) thymidine kinase (TK) gene, cytosine daminase, purine nucleoside phosphorylase, and nitroreductase.

An embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α $E.\ coli$ cells, Chinese hamster ovarian cells, monkey VERO cells, COS cells, HEK293 cells, and the like. For purposes of amplifying or replicating the recombinant expression vector, the host cell may be a prokaryotic cell, e.g., a DH5α cell. For purposes of producing a recombinant CAR, the host cell may be a mammalian cell. The host cell may be a human cell. While the host cell can be of any cell type, can originate from any type of tissue, and can be of any developmental stage, the host cell may be a peripheral blood lymphocyte (PBL) or a peripheral blood mononuclear cell (PBMC). The host cell may be a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, $CD4^+/CD8^+$ double positive T cells, $CD4^+$ helper T cells, e.g., $Th_1$ and $Th_2$ cells, $CD8^+$ T cells (e.g., cytotoxic T cells), tumor infiltrating cells, memory T cells, naïve T cells, and the like. The T cell may be a $CD8^+$ T cell or a $CD4^+$ T cell.

Also provided by an embodiment of the invention is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

In an embodiment of the invention, the numbers of cells in the population may be rapidly expanded. Expansion of the numbers of cells expressing the CAR can be accomplished by any of a number of methods as are known in the art as described in, for example, U.S. Pat. Nos. 8,034,334; 8,383, 099; U.S. Patent Application Publication No. 2012/0244133; Dudley et al., $J.\ Immunother.$, 26:332-42 (2003); and Riddell et al., $J.\ Immunol.\ Methods$, 128:189-201 (1990). In an embodiment, expansion of the numbers of cells is carried out by culturing the T cells with OKT3 antibody, IL-2, and feeder PBMC (e.g., irradiated allogeneic PBMC).

CARs, nucleic acids, recombinant expression vectors, and host cells (including populations thereof), all of which are collectively referred to as "inventive CAR materials" hereinafter, can be isolated and/or purified. The term "isolated" as used herein means having been removed from its natural environment. The term "purified" or "isolated" does not require absolute purity or isolation; rather, it is intended as a relative term. Thus, for example, a purified (or isolated) host cell preparation is one in which the host cell is more pure than cells in their natural environment within the body. Such host cells may be produced, for example, by standard purification techniques. In some embodiments, a preparation of a host cell is purified such that the host cell represents at least about 50%, for example at least about 70%, of the total cell content of the preparation. For example, the purity can be at least about 50%, can be greater than about 60%, about 70% or about 80%, or can be about 100%.

The inventive CAR materials can be formulated into a composition, such as a pharmaceutical composition. In this regard, an embodiment of the invention provides a pharmaceutical composition comprising any of the CARs, nucleic acids, expression vectors, and host cells (including populations thereof), and a pharmaceutically acceptable carrier. The inventive pharmaceutical compositions containing any of the inventive CAR materials can comprise more than one inventive CAR material, e.g., a CAR and a nucleic acid, or two or more different CARs. Alternatively, the pharmaceutical composition can comprise an inventive CAR material in combination with other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In a preferred embodiment, the pharmaceutical composition comprises the inventive host cell or populations thereof.

Preferably, the carrier is a pharmaceutically acceptable carrier. With respect to pharmaceutical compositions, the carrier can be any of those conventionally used for the particular inventive CAR material under consideration. Such pharmaceutically acceptable carriers are well-known to those skilled in the art and are readily available to the public. It is preferred that the pharmaceutically acceptable carrier be one which has no detrimental side effects or toxicity under the conditions of use.

The choice of carrier will be determined in part by the particular inventive CAR material, as well as by the particular method used to administer the inventive CAR material. Accordingly, there are a variety of suitable formulations of the pharmaceutical composition of the invention. Suitable formulations may include any of those for oral, parenteral, subcutaneous, intravenous, intramuscular, intraarterial, intrathecal, or interperitoneal administration. More than one route can be used to administer the inventive CAR materials, and in certain instances, a particular route can provide a more immediate and more effective response than another route.

Preferably, the inventive CAR material is administered by injection, e.g., intravenously. When the inventive CAR material is a host cell expressing the inventive CAR, the pharmaceutically acceptable carrier for the cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, IL), PLASMA-LYTE A (Baxter, Deerfield, IL), about 5% dextrose in water, or Ringer's lactate. In an embodiment, the pharmaceutically acceptable carrier is supplemented with human serum albumen.

The dose of the inventive CAR material also will be determined by the existence, nature and extent of any adverse side effects that might accompany the administration of a particular inventive CAR material. Typically, the attending physician will decide the dosage of the inventive CAR material with which to treat each individual patient, taking into consideration a variety of factors, such as age, body weight, general health, diet, sex, inventive CAR material to be administered, route of administration, and the severity of the cancer being treated. In an embodiment in which the inventive CAR material is a population of cells, the number of cells administered per infusion may vary, e.g., from about $1 \times 10^6$ to about $1 \times 10^{12}$ cells or more. In certain embodiments, fewer than $1 \times 10^6$ cells may be administered.

For purposes of the invention, the amount or dose of the inventive CAR material administered should be sufficient to effect a therapeutic or prophylactic response in the subject or animal over a reasonable time frame. For example, the dose of the inventive CAR material should be sufficient to bind to antigen, or detect, treat or prevent cancer in a period of from about 2 hours or longer, e.g., about 12 to about 24 or more hours, from the time of administration. In certain embodiments, the time period could be even longer. The dose will be determined by the efficacy of the particular inventive CAR material and the condition of the animal (e.g., human), as well as the body weight of the animal (e.g., human) to be treated.

For purposes of the invention, an assay, which comprises, for example, comparing the extent to which target cells are lysed and/or IFN-γ is secreted by T cells expressing the inventive CAR upon administration of a given dose of such T cells to a mammal, among a set of mammals of which is each given a different dose of the T cells, could be used to determine a starting dose to be administered to a mammal. The extent to which target cells are lysed and/or IFN-γ is secreted upon administration of a certain dose can be assayed by methods known in the art.

One of ordinary skill in the art will readily appreciate that the inventive CAR materials of the invention can be modified in any number of ways, such that the therapeutic or prophylactic efficacy of the inventive CAR materials is increased through the modification. For instance, the inventive CAR materials can be conjugated either directly or indirectly through a linker to a targeting moiety. The practice of conjugating compounds, e.g., inventive CAR materials, to targeting moieties is known in the art.

When the inventive CAR materials are administered with one or more additional therapeutic agents, one or more additional therapeutic agents can be coadministered to the mammal. By "coadministering" is meant administering one or more additional therapeutic agents and the inventive CAR materials sufficiently close in time such that the inventive CAR materials can enhance the effect of one or more additional therapeutic agents, or vice versa. In this regard, the inventive CAR materials can be administered first and the one or more additional therapeutic agents can be administered second, or vice versa. Alternatively, the inventive CAR materials and the one or more additional therapeutic agents can be administered simultaneously. An exemplary therapeutic agent that can be co-administered with the CAR materials is IL-2. It is believed that IL-2 enhances the therapeutic effect of the inventive CAR materials.

It is contemplated that the inventive pharmaceutical compositions, CARs, nucleic acids, recombinant expression vectors, host cells, or populations of cells can be used in methods of treating or preventing cancer in a mammal. Without being bound to a particular theory or mechanism, the inventive CARs have biological activity, e.g., ability to recognize antigen, e.g., CD70, such that the CAR when expressed by a cell is able to mediate an immune response against the cell expressing the antigen, e.g., CD70, for which the CAR is specific. In this regard, an embodiment of the invention provides a method of treating or preventing cancer in a mammal, comprising administering to the mammal the CARs, the nucleic acids, the recombinant expression vectors, the host cells, the population of cells, and/or the pharmaceutical compositions of the invention in an amount effective to treat or prevent cancer in the mammal.

An embodiment of the invention further comprises lymphodepleting the mammal prior to administering the inventive CAR materials. Examples of lymphodepletion include, but may not be limited to, nonmyeloablative lymphodepleting chemotherapy, myeloablative lymphodepleting chemotherapy, total body irradiation, etc.

For purposes of the inventive methods, wherein host cells or populations of cells are administered, the cells can be cells that are allogeneic or autologous to the mammal. Preferably, the cells are autologous to the mammal.

The mammal referred to herein can be any mammal. As used herein, the term "mammal" refers to any mammal, including, but not limited to, mammals of the order Rodentia, such as mice and hamsters, and mammals of the order Logomorpha, such as rabbits. The mammals may be from the order Camivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes). Preferably, the mammal is a human.

With respect to the inventive methods, the cancer can be any cancer, including any of acute lymphocytic cancer, acute myeloid leukemia, alveolar rhabdomyosarcoma, bladder cancer (e.g., bladder carcinoma), bone cancer, brain cancer (e.g., medulloblastoma), breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia (CLL), chronic myeloid cancer, colon cancer, esophageal cancer, cervical cancer, fibrosarcoma, gastrointestinal carcinoid tumor, head and neck cancer (e.g., head and neck squamous cell carcinoma), glioblastoma, Hodgkin's lymphoma, hypopharynx cancer, kidney cancer, larynx cancer, leukemia, liquid tumors, liver cancer, lung cancer (e.g., non-small cell lung carcinoma), lymphoma, diffuse large-B-cell lymphoma, follicular lymphoma, malignant mesothelioma, mastocytoma, melanoma, multiple myeloma, nasopharynx cancer, non-Hodgkin's lymphoma (NHL), B-chronic lymphocytic leukemia, hairy cell leukemia, acute lymphocytic leukemia (ALL), and Burkitt's lymphoma, ovarian cancer, pancreatic cancer, peritoneum, omentum, and mesentery cancer, pharynx cancer, prostate cancer, RCC, ccRCC, rectal cancer, renal cancer, skin cancer, small intestine cancer, soft tissue cancer, solid tumors, stomach cancer, testicular cancer, thyroid cancer, and ureter cancer. Preferably, the cancer is characterized by the expression of CD70. In a preferred embodiment, the cancer is any of RCC (for example, ccRCC), glioblastoma, NHL, CLL, diffuse large-B-cell lymphoma, and follicular lymphoma.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

Another embodiment of the invention provides a use of the inventive CARs, nucleic acids, recombinant expression vectors, host cells, populations of cells, or pharmaceutical compositions, for the treatment or prevention of cancer in a mammal.

Another embodiment of the invention provides a method of detecting the presence of cancer in a mammal, comprising: (a) contacting a sample comprising one or more cells from the mammal with the CARs, the nucleic acids, the recombinant expression vectors, the host cells, or the population of cells, of the invention, thereby forming a complex, (b) and detecting the complex, wherein detection of the complex is indicative of the presence of cancer in the mammal.

The sample may be obtained by any suitable method, e.g., biopsy or necropsy. A biopsy is the removal of tissue and/or cells from an individual. Such removal may be to collect tissue and/or cells from the individual in order to perform experimentation on the removed tissue and/or cells. This experimentation may include experiments to determine if the individual has and/or is suffering from a certain condition or disease-state. The condition or disease may be, e.g., cancer.

With respect to an embodiment of the inventive method of detecting the presence of cancer in a mammal, the sample comprising cells of the mammal can be a sample comprising whole cells, lysates thereof, or a fraction of the whole cell lysates, e.g., a nuclear or cytoplasmic fraction, a whole protein fraction, or a nucleic acid fraction. If the sample comprises whole cells, the cells can be any cells of the mammal, e.g., the cells of any organ or tissue, including blood cells or endothelial cells.

For purposes of the inventive detecting method, the contacting can take place in vitro or in vivo with respect to the mammal. Preferably, the contacting is in vitro.

Also, detection of the complex can occur through any number of ways known in the art. For instance, the inventive CARs, polypeptides, proteins, nucleic acids, recombinant expression vectors, host cells, or populations of cells, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

Methods of testing a CAR for the ability to recognize target cells and for antigen specificity are known in the art. For instance, Clay et al., *J. Immunol.*, 163: 507-513 (1999), teaches methods of measuring the release of cytokines (e.g., interferon-γ, granulocyte/monocyte colony stimulating factor (GM-CSF), tumor necrosis factor a (TNF-α) or interleukin 2 (IL-2)). In addition, CAR function can be evaluated by measurement of cellular cytotoxicity, as described in Zhao et al., *J Immunol.*, 174: 4415-4423 (2005).

The following examples further illustrate the invention but, of course, should not be construed as in any way limiting its scope.

EXAMPLE 1

This example demonstrates the transduction efficiency of a retroviral vector encoding a CAR including full-length mouse CD27 and a mouse CD3ζ T cell intracellular signaling domain (mCD27-CD3ζ CAR) and having the amino acid sequence of SEQ ID NO: 25 and the reactivity of the mCD27-CD3ζ CAR against mCD70-expressing tumor cells in vitro.

A retroviral vector encoding a CAR including full-length mouse CD27 and a mouse CD3ζ T cell intracellular signaling domain (mCD27-CD3ζ CAR) and having the amino acid sequence of SEQ ID NO: 25 was constructed. Murine T cells were retrovirally transduced with the mCD27-CD3ζ CAR retroviral vector. Transduction efficiency was determined to be 62.6%.

Mouse T cells generated from splenocytes were untransduced (UT) or transduced with a vector encoding GFP or the mCD27-CD3ζ CAR (effector cells) and cultured alone (medium) or co-cultured with B16 melanoma cells that do not express mouse CD70 (B16 cells) or B16 cells that were transduced to express mouse CD70 (B16/mCD70) target cells. Pmel cells, which are mouse T cells that recognize B16 tumor, were used as a positive control effector cell. IFN-γ secretion was measured. The results are shown in Table 2. As shown in Table 2, cells transduced with the mCD27-CD3ζ CAR showed high reactivity against CD70-expressing tumors in vitro.

TABLE 2

|  | IFN-γ (pg/ml) | | |
| --- | --- | --- | --- |
|  | B16 | B16/mCD70 | Medium |
| Medium | 0 | 0 | 0 |
| pmel | 795 | 1762 | 0 |
| Mouse T cells/UT | 0 | 0 | 0 |
| Mouse T cells/mGFP | 0 | 0 | 0 |
| Mouse T cells/ mCD27-CD3ζ CAR | 0 | 642122 | 0 |

EXAMPLE 2

This example demonstrates that mouse T cells generated from splenocytes transduced with a nucleotide sequence encoding a CAR including full-length mouse CD27 and a mouse CD3ζ T cell intracellular signaling domain (mCD27-CD3ζ CAR) and having the amino acid sequence of SEQ ID NO: 25 reduces tumor burden and increases the survival of CD70-expressing tumor-bearing mice.

Figure 1A:
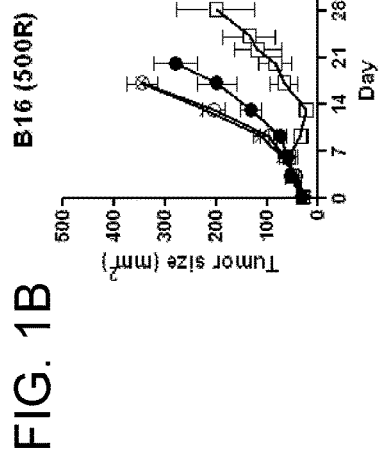
FIG. 1F is a graph showing the tumor size ($mm^2$) of B16/mCD70-tumor bearing mice over a period of time (days) following administration of mCD27-CD3ζ CAR-transduced cells (squares), untransduced cells (Δ), cells transduced with an empty vector (∇), or pmel+VI (circles), followed by irradiation and administration of IL-2.
Figure 1C:
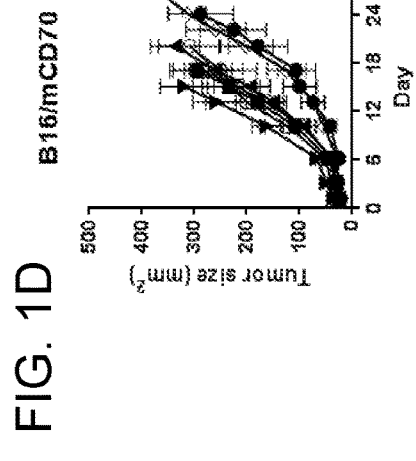
Figure 1E:
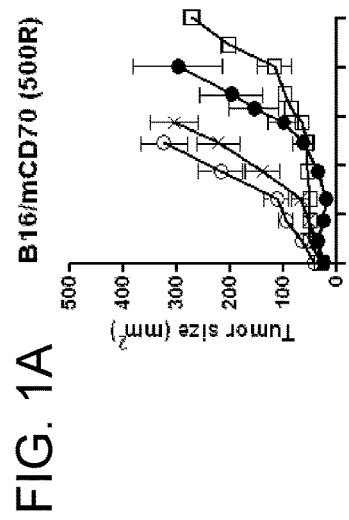
Figure 1B:
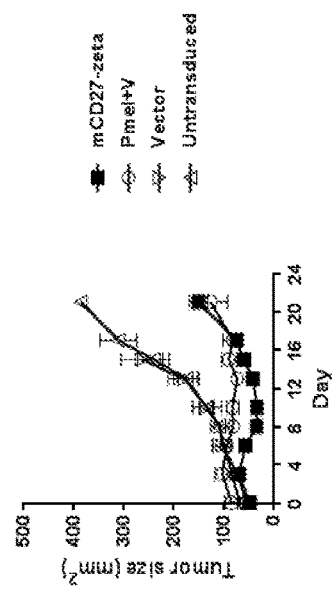

Eleven days prior to transferring CAR-expressing cells into mice, tumors were established in mice by injecting them with B16 cells or B16/mCD70 cells. Four days later, splenocytes were removed from the mice and stimulated with concanavalin A (ConA) and IL-7 or anti-mouse CD3 (mCD3) and soluble CD28 (sCD28). Two days later, mouse T cells generated from the stimulated splenocytes were transduced with a MSGV1 retroviral vector encoding the mCD27-CD3ζ CAR having the amino acid sequence of SEQ ID NO: 25. Five days later, the mCD27-CD3ζ CAR-transduced cells ($1 \times 10^7$) were administered to the tumor-bearing mice, and the mice were irradiated (500 rads). Control tumor-bearing mice were administered untransduced cells, phosphate buffered saline (PBS), or a combination of pmel cells (pmel), a gp100 vaccine (V), and IL-2 (I) ("pmel+VI") and irradiated. The size of the tumors was measured over a period of time up to about 35 days after treatment. The results are shown in FIGS. 1A-1B. As shown in FIGS. 1A-1B, the mCD27-CD3ζ CAR-transduced cells reduced the tumor burden in B16/mCD70-tumor bearing mice, but not in B16-tumor bearing mice. Accordingly, mice bearing CD70+ tumors could be successfully treated with mCD27-CD3ζ CAR-transduced cells, and the treatment was CD70-specific.

Figure 1D:
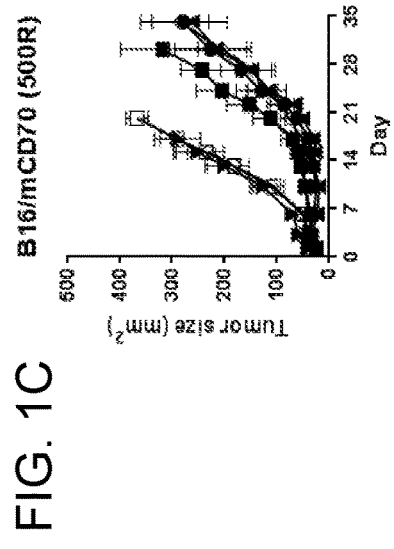
Figure 1F:
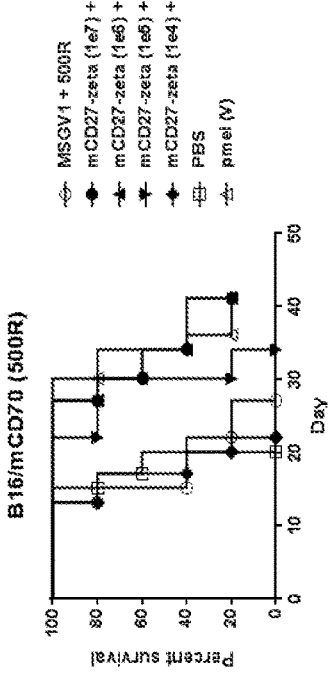

The experiment was repeated with B16/mCD70-tumor bearing mice, except that splenocytes were stimulated with anti-mCD3 and sCD28, and the mice were also administered IL-2 after irradiation and administration of transduced cells. Control tumor-bearing mice were administered untransduced cells, cells transduced with an empty vector, or pmel+VI, followed by irradiation and administration of IL-2. The size of the tumors was measured over a period of time up to about 24 days after treatment. The results are shown in FIG. 1F. As shown in FIG. 1F, when co-administered with IL-2, the mCD27-CD3ζ CAR-transduced cells reduced the tumor burden in B16/mCD70-tumor bearing mice.

Twenty-one days after cell transfer, the tumors were removed from the treated mice and grown in vitro for seven days. Mouse CD70 expression in the tumors was measured by FACS. It was observed that CD70 expression was lost in mice treated with mCD27-CD3ζ CAR-transduced cells but not in mice treated with Pmel+V or untransduced cells. Without being bound to a particular theory or mechanism, it is believed that recurrence of tumor growth was most likely due to the loss of CD70 expression on B16/mCD70 tumors.

The experiment corresponding to that of FIG. 1B was repeated again with B16/mCD70 tumor-bearing mice, with the following exceptions. B16/mCD70 tumor-bearing mice were administered mCD27-CD3ζ CAR-transduced cells at a dose of $1 \times 10^4$, $1 \times 10^5$, $1 \times 10^6$, or $1 \times 10^7$ cells per mouse with or without irradiation (500 Rads). Control tumor-bearing mice were administered PBS, pmel+VI, or mouse T cells that were transduced with an empty vector with or without irradiation (500 Rads). The results are shown in FIGS. 1C-1D. As shown in FIG. 1C, the lowest effective dose for treating tumors was $1 \times 10^5$ mCD27-CD3ζ CAR-transduced cells per mouse when mice were irradiated. As shown in FIGS. 1C-1D, at a dose of $1 \times 10^7$ cells per mouse, irradiation did not seem to affect treatment efficacy.

Survival of the tumor-bearing mice was also assessed over a period of time up to about 42 days after treatment. The results are shown in FIG. 1E. As shown in FIG. 1E, irradiated tumor-bearing mice treated with the mCD27-CD3ζ CAR-transduced cells survived longer, particularly at doses of $1 \times 10^6$ or $1 \times 10^7$ cells per mouse.

EXAMPLE 3

This example demonstrates that administration of cells transduced with the mCD27-CD3ζ CAR to tumor-bearing mice results in some toxicity. This example also demonstrates that the mice can recover from the toxicity.

B16 or B16/mCD70-tumor bearing mice were administered untransduced cells or cells transduced with the mCD27-CD3ζ CAR having the amino acid sequence of SEQ ID NO: 25, PBS, or pmel+V, with or without irradiation (500 Rads). The average weight of the mice was measured over a period beginning about six days after cell transfer up to about 17 days following treatment. The results are shown in FIGS. 2A-2D. As shown in FIGS. 2A-2D, transient lower body weights were observed for both B16/mCD70 and B16-tumor bearing mice that were treated with the mCD27-CD3ζ CAR. The lower body weight observed in the mCD27-CD3ζ CAR-treated mice was irrelevant to implanted tumors. Without being bound to a particular theory or mechanism, it is believed that the lower body weight implies that endogenous cells were targeted by the mCD27-CD3ζ CAR. The mice recovered lost body weight when they were administered a hydrogel containing water, hydrocolloids, food acid, and sodium benzoate.

B16 or B16/mCD70-tumor bearing mice were administered untransduced cells or cells transduced with the mCD27-CD3ζ CAR having the amino acid sequence of SEQ ID NO: 25, or cells transduced with a vector encoding GFP, with or without irradiation (500 Rads). The absolute white blood cell (WBC) count in the mice was measured over a period beginning about six days after cell transfer up to about 14 days following treatment. The results are shown in FIGS. 2E-2H. As shown in FIGS. 2E-2F, a transient lower WBC count was observed in the mice that were treated with the mCD27-CD3ζ CAR. As shown in FIGS. 2G-2H, a transient lower splenocyte count was also observed in the mice that were treated with the mCD27-CD3ζ CAR.

B16/mCD70-tumor bearing mice were administered cells transduced with the mCD27-CD3ζ CAR having the amino acid sequence of SEQ ID NO: 25 or cells transduced with a vector encoding GFP, with or without irradiation (500 Rads). Serum IFN-γ levels were measured for a period beginning about three days after cell transfer up to about seven days after treatment. The results are shown in FIG. 21. As shown in FIG. 21, transient IFN-γ secretion was observed in the irradiated mice treated with the mCD27-CD3ζ CAR.

EXAMPLE 4

This example demonstrates that administration of the mCD27-CD3ζ CAR does not have a measurable effect on the long-term immune function of non-tumor bearing mice.

Non-tumor bearing mice were administered cells that were transduced with the mCD27-CD3ζ CAR having the amino acid sequence of SEQ ID NO: 25 or cells transduced with a vector encoding GFP (GFP), with or without irradiation (500 Rads). The mice were immunized with ovalbumin (OVA) or human (h) gp100 32 or 50 days after transfer of transduced cells. T cells were removed from the spleen and lymph node (LN) of the mice seven days after immunization. The cells were stimulated in vitro with OT-1, OT-II, or hgp100 peptide. The results are shown in Table 3 (Day 32—spleen), Table 4 (Day 32—LN), and Table 5 (Day 50—spleen). In Table 5, immunized C57BL/6 (immune competent) mice (B6/Im) were used as a positive control. Naïve C57BL/6 mice (B6/naive) were used as a negative control. As shown in Tables 3-5, administration of the mCD27-CD3ζ CAR does not have a measurable effect on the long-term immune function of non-tumor bearing mice.

The histology of various organs, including brain, lung, liver, kidney, intestine, heart, spleen, and bone were examined from 3 days to 7 days after cell transfer. The chemistry of the blood, in particular, the blood levels of sodium, potassium, chloride, calcium, magnesium, phosphorus, glucose, blood urea nitrogen (BUN), creatinine, uric acid, albumin, protein, cholesterol, triglycerides, alkaline phosphatase (ALK P), alanineaminotransferase (ALT/GPT), aspartate aminotransferase (AST/GOT), amylase, creatine kinase (CK), and lactate dehydrogenase (LD) were examined from 3 days to 7 days after cell transfer. No changes in histology or blood chemistry were observed.

TABLE 3

| Immunized with: Stimulated | OVA | | | | hgp100 | |
|---|---|---|---|---|---|---|
| With: | OT-1 | | OT-II | | hgp100 | |
| mCD27-CD3ζ CAR (500 Rads) | 2263 | 54 | 44 | 48 | 1293 | <32 |
| GFP (500 Rads) | 1130 | 84 | 67 | 60 | 177 | 40 |
| mCD27-CD3ζ CAR | 347 | <32 | <32 | <32 | 298 | <32 |
| GFP | 933 | 96 | 96 | 93 | 544 | 80 |

TABLE 4

| Immunized with: Stimulated | OVA | | | | hgp100 | |
|---|---|---|---|---|---|---|
| With: | OT-1 | | OT-II | | hgp100 | |
| mCD27-CD3ζ CAR (500 Rads) | <32 | <32 | 12980 | <32 | <35 | <32 |
| GFP (500 Rads) | 62 | <32 | 230 | <32 | <35 | 45 |
| mCD27-CD3ζ CAR | 235 | 66 | 557 | 32 | 301 | 139 |
| GFP | 121 | <32 | 340 | 35 | <35 | <32 |

TABLE 5

| Immunized with: Stimulated | OVA | | | | hgp100 | |
|---|---|---|---|---|---|---|
| With: | OT-1 | | OT-II | | hgp100 | |
| mCD27-CD3ζ CAR (500 Rads) | 1708 | 24 | 575 | <32 | <32 | <32 |
| GFP (500 Rads) | 498 | 114 | 4429 | 122 | <32 | <32 |
| mCD27-CD3ζ CAR | 1219 | 77 | 995 | <32 | <32 | <32 |
| GFP | 371 | <32 | 370 | <32 | 67 | <32 |
| B6/Im | 1138 | 79 | 245 | 39 | 119 | 33 |
| B6/naive | <32 | <32 | 134 | 70 | <32 | <32 |

EXAMPLE 5

This example demonstrates that T cells transduced with a nucleotide sequence encoding a CAR including full-length human CD27 and a human CD3ζ T cell intracellular signaling domain (fCD27-CD3ζ CAR) express the CAR following expansion of the numbers of transduced cells.

PBL were non-specifically stimulated with OKT3 and T cells generated from the PBL were (a) untransduced (UT), (b) transduced with a nucleotide sequence encoding full-length human CD27 (fCD27), or (c) transduced with a nucleotide sequence encoding the fCD27-CD3ζ CAR having the amino acid sequence of SEQ ID NO: 7. The cells were grown, analyzed for CAR expression by fluorescence-activated cell sorting (FACS), and tested for tumor reactivity based on IFN-γ production. The numbers of CD70-reactive cells were rapidly expanded (REP) generally as described in Riddell et al., J Immunol. Methods, 128: 189-201 (1990). Expanded numbers of cells were grown and analyzed for expression of CD27, CD70, CD45RO, and CD62L by FACS. Table 6 shows the percentage of cells with the indicated phenotypes as measured by FACS. Table 7 shows the fold expansion and viability (%) of the cells following stimulation (but before REP) and after REP. As shown in Tables 6 and 7, expanded numbers of transduced cells express the CAR and are viable and have an effector memory phenotype.

TABLE 6

| | | UT | fCD27 | fCD27-CD3ζ CAR |
|---|---|---|---|---|
| After | CD27+/CD70+ | 10.84% | 2.04% | 3.27% |

TABLE 6-continued

|  |  | UT | fCD27 | fCD27-CD3ζ CAR |
|---|---|---|---|---|
| stimulation and before REP | CD27−/CD70+ | 25.85% | 0.53% | 0.36% |
|  | CD27+/CD70− | 44.82% | 85.18% | 94.55% |
|  | CD27−/CD70− | 18.49% | 12.24% | 1.82% |
|  | CD45RO+/CD62L+ | 48.97% | 29.02% | 39.77% |
|  | CD45RO−/CD62L+ | 8.14% | 7.38% | 6.50% |
|  | CD45RO+/CD62L− | 31.70% | 48.63% | 47.27% |
|  | CD45RO−/CD62L− | 11.19% | 14.97% | 6.47% |
| After REP | CD27+/CD70+ | 5.20% | 4.93% | 0.45% |
|  | CD27−/CD70+ | 70.02% | 12.53% | 0.12% |
|  | CD27+/CD70− | 11.01% | 71.76% | 91.84% |
|  | CD27−/CD70− | 13.77% | 10.78% | 7.59% |
|  | CD45RO+/CD62L+ | 17.42% | 14.52% | 12.39% |
|  | CD45RO−/CD62L+ | 2.40% | 1.59% | 5.53% |
|  | CD45RO+/CD62L− | 72.9% | 73.98% | 44.37% |
|  | CD45RO−/CD62L− | 7.40% | 9.90% | 37.70% |

TABLE 7

|  |  | Fold expansion | Viability (%) |
|---|---|---|---|
| After stimulation and before REP | UT | 6 | 88 |
|  | fCD27 | 3 | 84 |
|  | fCD27-CD3ζ CAR | 3 | 70 |
| After REP | UT | 720 | 86 |
|  | fCD27 | 560 | 75 |
|  | fCD27-CD3ζ CAR | 790 | 79 |

EXAMPLE 6

This example demonstrates that T cells transduced with a nucleotide sequence encoding a CAR including full-length human CD27 and a human CD3ζ T cell intracellular signaling domain (fCD27-CD3ζ CAR) proliferate upon co-culture with CD70-expressing cells and specifically recognize CD70-expressing tumor cell lines in vitro.

T cells were generated from human PBL. Untransduced (UT) T cells or T cells transduced with a nucleotide sequence encoding fCD27 or the fCD27-CD3ζ CAR (effector cells) were cultured alone or co-cultured with CD70-expressing tumor cell line 624mel or 624mel cells transduced with CD70 (624/CD70) (target cells). Proliferation of the effector cells was measured using carboxyfluorescein succinimidyl ester (CFSE) on day 4 of the co-culture. The T cells transduced with the fCD27-CD3ζ CAR proliferated only when co-cultured with the CD70-expressing tumor cell line 624/CD70. The UT T cells and the T cells transduced with fCD27 did not proliferate in any culture.

UT T cells or T cells transduced with a nucleotide sequence encoding fCD27 or the fCD27-CD3ζ CAR (SEQ ID NO: 7) (effector cells) were cultured alone (medium) or co-cultured with one of the human RCC cell lines or control cell lines 624, 624/CD70, SNU245, SNU1079, or SNU1196 (target cells) shown in Table 8 below. All SNU cell lines were CD70 negative. IFN-γ secretion was measured. The results are shown in Table 8. As shown in Table 8, T cells transduced with a nucleotide sequence the fCD27-CD3ζ CAR (SEQ ID NO: 7) were reactive against CD70-expressing human RCC cell lines.

TABLE 8

|  |  | IFN-γ (pg/ml) | | |
|---|---|---|---|---|
|  | CD70 expression | UT | fCD27 | fCD27-CD3ζ CAR |
| 624 | Negative (Neg) | 39 | 170 | 87 |
| 624/CD70 | Positive (Pos) | 29 | 173 | 6485 |
| RCC 2219R | Pos | 61 | 147 | 12068 |
| RCC 2245R | Pos | 29 | 103 | 9108 |
| RCC 2095R | Pos | 40 | 210 | 5819 |
| RCC 1581 | Pos | 41 | 163 | 11797 |
| RCC 2246R | Pos | 27 | 94 | 8221 |
| RCC 2657R | Pos | 17 | 48 | 3510 |
| RCC 2361R | Pos | 14 | 48 | 2256 |
| RCC 2261R | Pos | 60 | 129 | 7267 |
| RCC 2654R | Pos | 38 | 150 | 7894 |
| SNU245 | Neg | 86 | 150 | 36 |
| SNU1079 | Neg | 70 | 110 | 33 |
| SNU1196 | Neg | 35 | 85 | 25 |
| Medium | — | 185 | 389 | 53 |

EXAMPLE 7

This example demonstrates the transduction efficiency of anti-CD70 human CAR constructs.

Human T cells were transduced with an empty retroviral vector (Mock) or a retroviral vector encoding one of the constructs set forth in Tables 9A-9C. CARs including a truncated (Δ) CD27 lack all of the CD27 intracellular T cell signaling domain, that is, the truncated CD27 lacks contiguous amino acid residues 212-260 of SEQ ID NO: 2. Transduced cells were analyzed for CD3, CD27, CD62L, and CD45RO expression by FACS. Tables 9A-9C show the percentage of cells with the indicated phenotypes as measured by FACS. As shown in Table 9B, cells transduced with CARs have an effector memory phenotype.

TABLE 9A

|  | Phenotype (%) | | | |
|---|---|---|---|---|
|  | CD3+/ CD27+ | CD3+/ CD27− | CD3−/ CD27+ | CD3−/ CD27− |
| full length (f) CD27-CD3ζ (SEQ ID NO: 7) | 75.90 | 5.85 | 16.00 | 2.23 |
| truncated (Δ) CD27-CD28 - CD3ζ (SEQ ID NO: 8) | 44.30 | 51.60 | 0.70 | 3.41 |
| ΔCD27-4-1BB - CD3ζ (SEQ ID NO: 9) | 60.20 | 27.90 | 8.16 | 3.71 |
| ΔCD27-CD28 - 4-1BB - CD3ζ (SEQ ID NO: 10) | 16.0 | 80.30 | 0.30 | 3.39 |
| fCD27-CD28 - CD3ζ (SEQ ID NO: 11) | 3.11 | 93.90 | 0.037 | 2.98 |
| fCD27-4-1BB - CD3ζ (SEQ ID NO: 12) | 60.70 | 29.20 | 5.98 | 4.10 |
| fCD27-CD28 - 4-1BB-CD3ζ (SEQ ID NO: 13) | 60.80 | 23.40 | 9.66 | 6.08 |
| Mock (control) (empty vector) | 0.26 | 97.50 | $6.75 \times 10^{-3}$ | 2.28 |

TABLE 9B

| | Phenotype (%) | | | |
|---|---|---|---|---|
| | CD45RO+/ CD62L+ | CD45RO+/ CD62L- | CD45RO-/ CD62L+ | CD45RO-/ CD62L- |
| full length (f) CD27-CD3ζ (SEQ ID NO: 7) | 68.30 | 23.50 | 6.13 | 2.03 |
| truncated (Δ) CD27-CD28 - CD3ζ (SEQ ID NO: 8) | 84.70 | 9.52 | 4.49 | 1.25 |
| ΔCD27-4-1BB - CD3ζ (SEQ ID NO: 9) | 74.00 | 20.20 | 4.20 | 1.60 |
| ΔCD27-CD28 - 4-1BB - CD3ζ (SEQ ID NO: 10) | 86.40 | 7.83 | 4.54 | 1.19 |
| fCD27-CD28 - CD3ζ (SEQ ID NO: 11) | 87.70 | 9.72 | 1.76 | 0.86 |
| fCD27-4-1BB - CD3ζ (SEQ ID NO: 12) | 69.10 | 22.70 | 5.80 | 2.35 |
| fCD27-CD28 - 4-1BB - CD3ζ (SEQ ID NO: 13) | 73.20 | 13.90 | 10.20 | 2.72 |
| Mock (control) (empty vector) | 85.50 | 11.60 | 2.11 | 0.73 |

TABLE 9C

| | Phenotype (%) | | | |
|---|---|---|---|---|
| | CD27+/ CD70+ | CD27+/ CD70- | CD27-/ CD70+ | CD27-/ CD70- |
| full length (f) CD27-CD3ζ (SEQ ID NO: 7) | 1.63 | 96.40 | 0.10 | 1.89 |
| truncated (Δ) CD27-CD28 - CD3ζ (SEQ ID NO: 8) | 0.69 | 90.80 | 0.46 | 8.06 |
| ΔCD27-4-1BB - CD3ζ (SEQ ID NO: 9) | 0.77 | 95.40 | 0.057 | 3.77 |
| ΔCD27-CD28 - 4-1BB - CD3ζ (SEQ ID NO: 10) | 0.42 | 83.80 | 0.66 | 15.10 |
| fCD27-CD28 - CD3ζ (SEQ ID NO: 11) | 9.30 | 68.10 | 11.60 | 11.0 |
| fCD27-4-1BB - CD3ζ (SEQ ID NO: 12) | 1.09 | 92.20 | 0.16 | 6.55 |
| fCD27-CD28 - 4-1BB - CD3ζ (SEQ ID NO: 13) | 2.04 | 92.70 | 0.11 | 5.18 |
| Mock (control) (empty vector) | 1.67 | 28.50 | 51.30 | 18.50 |

EXAMPLE 8

This example demonstrates that human T cells transduced with f CD27-CD3ζ (SEQ ID NO: 7), ΔCD27-4-1BB—CD3ζ (SEQ ID NO: 9), ΔCD27-CD28—4-1BB—CD3ζ (SEQ ID NO: 10), fCD27-4-1BB—CD3ζ (SEQ ID NO: 12), or fCD27-CD28—4-1BB—CD3ζ (SEQ ID NO: 13) recognize CD70-expressing RCC tumor cells in vitro.

Human T cells were transduced with an empty retroviral vector (MSGV1) or a retroviral vector encoding one of the constructs set forth in Table 9A. Transduced cells were cultured alone (medium) or co-cultured with control target cells 624mel, 624/CD70, 938mel, or 938mel cells transduced to express CD70 (938/CD70) or RCC target cells RCC 2245R, RCC 2246R, RCC 2361R, or RCC 1764. IFN-γ secretion was measured. The results are shown in FIG. 3. As shown in FIG. 3, human T cells transduced with fCD27-CD3ζ (SEQ ID NO: 7), ΔCD27-4-1BB—CD3ζ (SEQ ID NO: 9), ΔCD27-CD28—4-1BB—CD3ζ (SEQ ID NO: 10), fCD27-4-1BB—CD3ζ (SEQ ID NO: 12), or fCD27-CD28—4-1BB—CD3ζ (SEQ ID NO: 13) recognize CD70-expressing RCC tumor cells in vitro.

EXAMPLE 9

This example demonstrates the selection of a ΔCD27-4-1BB—CD3ζ (SEQ ID NO: 9) retroviral-vector producing packaging clone.

Retroviral packaging cell line PG13 clones A2, A10, B3, C1, E3, G2, were untransduced or transduced with a retroviral vector encoding ΔCD27-4-1BB—CD3ζ (SEQ ID NO: 9). Table 10 shows the percentage of cells with the indicated phenotypes as measured by FACS.

TABLE 10

| | Phenotype (%) | | | |
|---|---|---|---|---|
| | CD3+/ CD27+ | CD3-/ CD27+ | CD3+/ CD27- | CD3-/ CD27- |
| A2 | 32.6 | 0.30 | 65.9 | 1.16 |
| A10 | 31.0 | 0.34 | 67.7 | 0.94 |
| B3 | 27.6 | 0.25 | 71.2 | 0.91 |
| C1 | 30.0 | 0.33 | 68.7 | 0.94 |
| E3 | 40.9 | 0.40 | 57.8 | 0.95 |
| G2 | 18.6 | 0.17 | 80.3 | 0.95 |
| Untransduced (UT) | 0.12 | 0.020 | 98.6 | 1.28 |

The transduced clones were cultured alone (medium) or co-cultured with target control cells 938mel, 938/CD70, SNU1079, SNU1196, or target RCC cell lines RCC 2245R, RCC 2246R, RCC 2361R, or RCC 1764. IFN-γ secretion was measured. The results are shown in FIG. 4. As shown in FIG. 4, retroviral packaging clone E3 demonstrated reactivity against CD70-expressing target tumor cell lines.

Retroviral packaging cell clones were transduced with a CAR as set forth in Table 11. Table 11 shows the percentage of cells with the indicated phenotypes as measured by FACS.

TABLE 11

| | Phenotype (%) | | | |
|---|---|---|---|---|
| | CD3+/ CD27+ | CD3-/ CD27+ | CD3+/ CD27- | CD3-/ CD27- |
| PG13/B11/fCD27-CD3ζ (SEQ ID NO: 7) | 73.5 | 1.37 | 24.5 | 0.62 |
| PG13/A2/ΔCD27-4-1BB - CD3ζ (SEQ ID NO: 9) | 34.7 | 0.57 | 63.5 | 1.18 |
| PG13/E3/ΔCD27-4-1BB - CD3ζ (SEQ ID NO: 9) | 50.7 | 1.23 | 47.0 | 1.07 |
| PG13/C5/fCD27-CD28 - 4-1BB - CD3ζ (SEQ ID NO: 13) | 45.7 | 1.48 | 51.4 | 1.43 |
| RD114/D2/fCD27-CD28 - | 30.7 | 0.65 | 67.8 | 0.91 |

TABLE 11-continued

| | Phenotype (%) | | | |
|---|---|---|---|---|
| | CD3+/ CD27+ | CD3−/ CD27+ | CD3+/ CD27− | CD3−/ CD27− |
| 4-1BB - CD3ζ (SEQ ID NO: 13) Untransduced (UT) | 0.26 | 3.45 × 10⁻³ | 98.9 | 1.71 |

The transduced clones were cultured alone (medium) or co-cultured with target control cells 938mel, 938/CD70, SNU1079, SNU1196, or target RCC cell lines RCC 2245R, RCC 2246R, RCC 2361R, or RCC 1764. IFN-γ secretion was measured. The results are shown in FIG. 5. As shown in FIG. 5, retroviral packaging clone E3 demonstrated reactivity against CD70-expressing target tumor cell lines.

Based on its transduction efficiency and tumor activity, retroviral packaging clone E3/ΔCD27-4-1BB—CD3ζ (SEQ ID NO: 9) was chosen for clinical use.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A chimeric antigen receptor (CAR) having antigenic specificity for CD70, wherein the CAR comprises the amino acid sequence of SEQ ID NO: 12, and wherein CD70 comprises the amino acid sequence of SEQ ID NO: 1.

2. A nucleic acid comprising a nucleotide sequence encoding the CAR of claim 1.

3. A nucleic acid comprising a nucleotide sequence encoding a chimeric antigen receptor (CAR) having antigenic specificity for CD70, wherein the nucleic acid comprises the nucleotide sequence of SEQ ID NO: 19, and wherein CD70 comprises the amino acid sequence of SEQ ID NO: 1.

4. A recombinant expression vector comprising the nucleic acid of claim 3.

5. An isolated host cell comprising the recombinant expression vector of claim 4.

6. A population of host cells comprising two or more host cells of claim 5.

7. A pharmaceutical composition comprising (i) the CAR of claim 1, (ii) a nucleic acid comprising a nucleotide sequence encoding the CAR of (i), (iii) a recombinant expression vector comprising the nucleic acid of (ii), (iv) a host cell comprising the recombinant expression vector of (iii), or (v) a population of host cells comprising two or more host cells of (iv), and a pharmaceutically acceptable carrier.

* * * * *